United States Patent [19]

Cartwright et al.

[11] 4,285,723

[45] Aug. 25, 1981

[54] SELECTIVE HERBICIDES

[75] Inventors: David Cartwright, Reading; David J. Collins, Crowthorne, both of England

[73] Assignee: Imperial Chemical Industries Limited, London, England

[21] Appl. No.: 57,005

[22] Filed: Jul. 12, 1979

Related U.S. Application Data

[63] Continuation-in-part of Ser. No. 642, Jan. 2, 1979, abandoned.

[30] Foreign Application Priority Data

Jan. 19, 1978 [GB] United Kingdom ............... 2237/78
May 30, 1978 [GB] United Kingdom ............. 23772/78

[51] Int. Cl.³ .................... A01N 41/06; C07C 143/74; C07C 143/78
[52] U.S. Cl. ......................... 71/103; 564/84; 564/97; 564/99; 260/465 D
[58] Field of Search ................. 71/103; 260/556 AC, 260/556 A, 465 D, 556 AR, 556 F; 564/84, 97, 99, 80

[56] References Cited

U.S. PATENT DOCUMENTS

| | | | |
|---|---|---|---|
| 3,622,626 | 11/1971 | Moore | 260/556 AC X |
| 3,689,523 | 9/1972 | Trancik et al. | 260/556 AC X |
| 3,840,597 | 10/1974 | Moore et al. | 260/556 AC X |
| 3,873,303 | 3/1975 | Theissen | 71/118 |
| 3,906,024 | 9/1975 | Moore et al. | 71/103 X |
| 3,928,416 | 12/1975 | Bayer et al. | 260/471 R |
| 4,063,929 | 12/1977 | Bayer et al. | 156/453 |
| 4,164,408 | 8/1979 | Theissen | 71/103 X |
| 4,164,409 | 8/1979 | Theissen | 71/103 X |
| 4,164,410 | 8/1979 | Theissen | 71/103 X |

FOREIGN PATENT DOCUMENTS

| | | |
|---|---|---|
| 315147 | 5/1974 | Austria . |
| 2753900 | 8/1978 | Fed. Rep. of Germany . |
| 7729708 | 4/1978 | France . |

Primary Examiner—Catherine L. Mills
Attorney, Agent, or Firm—Cushman, Darby & Cushman

[57] ABSTRACT

Herbicidal diphenyl ether compounds of the formula

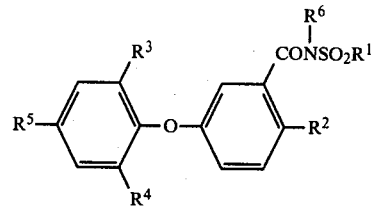

wherein $R^1$ is an alkyl group optionally substituted by halogen or phenyl; $R^2$ is hydrogen, halogen or nitro; $R^3$ is hydrogen, halogen, alkyl, trifluoromethyl or cyano; $R^4$ is hydrogen, halogen, or trifluoromethyl; $R^5$ is halogen or trifluoromethyl; and $R^6$ is hydrogen, or $C_1$–$C_4$ alkyl. These compounds are useful as selective herbicides in a range of crops, for example, cotton, soya bean, peas, maize, wheat and rice.

9 Claims, No Drawings

SELECTIVE HERBICIDES

This application is a continuation-in-part of Ser. No. 642, filed Jan. 2, 1979, now abandoned.

This invention relates to diphenyl ether compounds useful as herbicides, and to herbicidal compositions and processes utilising them.

Many compounds of the diphenyl ether series have been proposed for use as herbicides. By way of examples of the large number of publications containing such proposals, there may be mentioned as an early example U.K. Pat. No. 974,475 and as a more recent example U.S. Pat. No. 3,928,416.

According to the present invention there are provided herbicidal diphenyl ether compounds of the formula (I):

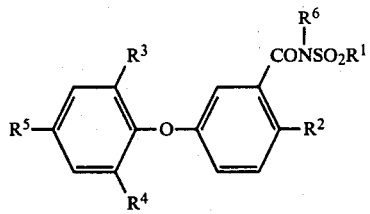

and salts thereof, wherein $R^1$ is an alkyl group optionally substituted by one or more fluorine atoms or by an optionally substituted phenyl group; $R^2$ is a hydrogen atom, a fluorine, chlorine, bromine or iodine atom, or a nitro group; $R^3$ is a hydrogen atom, a fluorine, chlorine, bromine, or iodine atom, an alkyl group, a trifluoromethyl group, or a cyano group; $R^4$ is a hydrogen atom, a fluorine, chlorine, bromine, or iodine atom, or a trifluoromethyl group; $R^5$ is a fluorine, chlorine, bromine, or iodine atom or a trifluoromethyl group; and $R^6$ is a hydrogen atom or an alkyl group of 1 to 4 carbon atoms.

When either of the groups $R^1$ and $R^3$ is an alkyl group, it may be an alkyl group of, for example, 1 to 12 or more carbon atoms. Within this range, $R^1$ and $R^3$ may be, for example, an alkyl group of one to six carbon atoms, for example a methyl, ethyl, propyl, isopropyl, butyl, isobutyl, sec-butyl or t-butyl group. When $R^1$ is an alkyl group substituted by phenyl it may be, for example, a benzyl group in which the phenyl radical may optionally be substituted, for example by one or more halogen atoms. When $R^1$ is a fluorine-substituted alkyl group, it may be for example an alkyl group of 1 to 6 carbon atoms substituted by one or more fluorine atoms; for example it may be a monofluoro-, difluoro-, or trifluoro-methyl group.

Compounds of the invention include, for example, those in which $R^1$ is a methyl or ethyl group, $R^2$ is a nitro group, $R^3$ is a chlorine atom, $R^4$ is a hydrogen atom, $R^5$ is a chlorine atom or a trifluoromethyl group, and $R^6$ is a hydrogen atom.

A further group of compounds of the invention are those in which $R^1$ is a methyl group; $R^2$ is a chlorine or bromine atom; $R^3$ is a chlorine atom; $R^4$ is a hydrogen atom; $R^5$ is a chlorine atom or a trifluoromethyl group; $R^6$ is a hydrogen atom.

Particular examples of compounds according to the invention are listed in Table 1 below.

TABLE 1

| COMPOUND NO | $R^1$ | $R^2$ | $R^3$ | $R^4$ | $R^5$ | $R^6$ | MELTING POINT °C. |
|---|---|---|---|---|---|---|---|
| 1 | CH$_3$ | NO$_2$ | Cl | H | CF$_3$ | H | 201 |
| 2 | C$_2$H$_5$ | NO$_2$ | Cl | H | CF$_3$ | H | 161.5 |
| 3 | C$_3$H$_7$ | NO$_2$ | Cl | H | CF$_3$ | H | 179 |
| 4 | C$_4$H$_9$ | NO$_2$ | Cl | H | CF$_3$ | H | 183 |
| 5 | C$_6$H$_{13}$ | NO$_2$ | Cl | H | CF$_3$ | H | 171 |
| 6 | CH$_3$ | NO$_2$ | Cl | H | CF$_3$ | CH$_3$ | 117 |
| 7 | CH$_3$ | Cl | Cl | H | CF$_3$ | H | 185.5 |
| 8 | CH$_3$ | Cl | Cl | H | CF$_3$ | CH$_3$ | 116 |
| 9 | CH$_3$ | Br | Cl | H | CF$_3$ | H | 164 |
| 10 | CH$_3$ | Br | Cl | H | CF$_3$ | CH$_3$ | 108 |
| 11 | CH$_3$ | H | Cl | H | CF$_3$ | H | 168 |
| 12 | C$_4$H$_9$ | H | Cl | H | CF$_3$ | H | 102 |
| 13 | CH$_2$C$_6$H$_5$ | H | Cl | H | CF$_3$ | H | 186.5 |
| 14 | CH$_3$ | H | H | H | CF$_3$ | H | 124.5–126 |
| 15 | CH$_3$ | H | CN | H | CF$_3$ | H | 198–199 |
| 16 | CH$_3$ | NO$_2$ | CN | H | CF$_3$ | H | 171–172 |
| 17 | CH$_3$ | NO$_2$ | Cl | H | Cl | H | 182–183 |
| 18 | C$_4$H$_9$ | NO$_2$ | Cl | H | Cl | H | 198–200 |
| 19 | CH$_3$ | H | Cl | H | Cl | H | 184–187 |
| 20 | CH$_3$ | Br | Cl | H | Cl | H | 146–147 |
| 21 | CH$_3$ | NO$_2$ | Cl | Cl | Cl | H | 227.5–228 |
| 22 | CH$_3$ | NO$_2$ | Br | Br | Br | H | 237–239 |
| 23 | CH$_3$ | NO$_2$ | CH$_3$ | H | Cl | H | 177.5–178.5 |
| 24 | isoC$_3$H$_7$ | NO$_2$ | Cl | H | CF$_3$ | H | 146 |
| 25 | CH$_3$ | H | CF$_3$ | H | Cl | H | 129–130 |
| 26 | CF$_3$ | NO$_2$ | Cl | H | CF$_3$ | H | 100 |
| 27 | C$_3$H$_7$ | Cl | Cl | H | CF$_3$ | H | 146 |
| 28 | C$_4$H$_9$ | Cl | Cl | H | CF$_3$ | H | 149.5 |
| 29 | CH$_3$ | NO$_2$ | F | Cl | Cl | H | 148–150 |
| 30 | CH$_3$ | I | Cl | H | CF$_3$ | H | 165–166 |
| 31 | CH$_3$ | NO$_2$ | Cl | CH$_3$ | Cl | H | 203–204 |
| 32 | CH$_3$ | NO$_2$ | Cl | H | F | H | 162–163 |
| 33 | CH$_3$ | F | Cl | H | CF$_3$ | H | 157–158 |
| 34 | CH$_3$ | NO$_2$ | Br | F | Br | H | 167–169.5 |
| 35 | CH$_3$ | H | Cl | H | Br | H | 184–185.5 |
| 36 | CH$_3$ | NO$_2$ | Br | H | CF$_3$ | H | 163–167 |
| 37 | CH$_3$ | NO$_2$ | H | H | CF$_3$ | H | 165–168 |
| 38 | CH$_3$ | NO$_2$ | F | H | CF$_3$ | H | 194–195 |
| 39 | CH$_3$ | NO$_2$ | CF$_3$ | H | CF$_3$ | H | 170–171 |
| 40 | CH$_3$ | NO$_2$ | Cl | Cl | Br | H | 196–199 |
| 41 | CH$_3$ | NO$_2$ | CF$_3$ | H | Cl | H | 155 |
| 42 | CH$_3$ | NO$_2$ | Cl | Cl | CF$_3$ | H | 242–243 |
| 43 | CH$_3$ | NO$_2$ | I | H | CF$_3$ | H | 208 |
| 44 | CH$_3$ | NO$_2$ | Cl | F | CF$_3$ | H | 163 |
| 45 | CH$_3$ | NO$_2$ | Cl | Br | CF$_3$ | H | 244–245 |

Further examples of compounds falling within the scope of the invention include the following:

2-chloro-5-(2,6-dichloro-4-trifluoromethylphenoxy)-N-methanesulphonylbenzamide 5-(2,4-dibromophenoxy)-2-nitro-N-methanesulphonylbenzamide 5-(2-chloro-6-fluoro-4-trifluoromethylphenoxy)-2-chloro-N-methanesulphonylbenzamide 5-(4-bromo-2-chlorophenoxy)-2-nitro-N-methanesulphonylbenzamide 5-(2,6-difluoro-4-trifluoromethylphenoxy)-2-nitro-N-methanesulphonylbenzamide Where the group $R^6$ is a hydrogen atom, it is possible to write an alternative structure for the compounds of the invention in which this hydrogen atom is attached not to the nitrogen atom but to the oxygen atom of the adjacent carbonyl group, with consequent re-arrangement of the chemical bonds of the molecule. This alternative structure, which is tautomeric with the structure drawn above, is shown below.

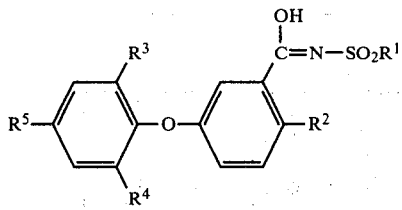

The spectral properties of the compounds of the invention indicate that they have the structure drawn as formula (I) and not the alternative structure shown last above. The structural formulae given in this specification are nevertheless intended to be inclusive of and representative of such tautomeric structures, to the extent that they may occur. The structural formulae are also intended to include physically distinguishable modifications of the compounds which may arise, for example, from different ways in which the molecules are arranged in a crystal lattice, or from the inability of parts of the molecule to rotate freely in relation to other parts, or from geometrical isomerism, or from intramolecular or inter-molecular hydrogen bonding, or otherwise.

Compounds of the invention wherein the group $R^6$ is a hydrogen atom are acids and form salts with bases. Both the acid and the salt forms of the compounds may be used as herbicides. Examples of salts include metal salts and salts formed from ammonium and substituted ammonium cations. Among the metal salts are those in which the metal cation is an alkali metal cation, for example sodium, potassium, or lithium, or an alkaline earth metal cation, for example calcium or magnesium. The substituted ammonium cations include mono-, di-, tri- and tetrasubstituted ammonium cations in which the substituents may be for example an alkyl or alkenyl radical of 1 to 20 carbon atoms optionally containing one or more hydroxy, alkoxy or phenyl substituents. Particular examples of substituted ammonium cations include isopropylammonium, triethanolammonium, benzyltrimethylammonium, morpholinium, piperidinium, trimethylammonium, triethylammonium, methoxyethylammonium, dodecylammonium and octadecylammonium, and the ammonium salts derived from the commercially available mixtures of amines sold under the Trade Names Armeen 12D, Armeen 16D, Armeen 18D, Armeen C, Armeen S, Armeen T and Armeen O.

The compounds of the invention may exhibit polymorphism; that is to say, a particular compound may exist in more than one physically distinguishable form in the solid state. Thus, it has been observed that when compound 1 is prepared and recrytallised by the methods described in Examples 1 and 2, the product obtained has an absorption peak at 1680 cm$^{-1}$ in its infra-red spectrum which is assigned to the amide carbonyl group. If this material is dissolved in dilute sodium hydroxide solution, and then re-precipitated by acidification, the product obtained after washing the precipitate with water and drying has an infra-red spectrum in which the absorption peak attributed to the amide carbonyl group has shifted to 1708 cm$^{-1}$. It is believed that the difference in the infra-red spectra may be due to differences in hydrogen bonding in the two materials. In the form with absorption at 1680 cm$^{-1}$ the hydrogen of the NH group is believed to be bonded to the oxygen of a carbonyl group in an adjacent, separate molecule. In the form with absorption at 1708 cm$^{-1}$, the hydrogen of the NH group is believed to be bonded within the molecule itself, to one of the oxygen atoms in the adjacent nitro group. It is believed that these differences in hydrogen bonding could also account for a variability in melting point which has been observed with compound no 1. Melting points from 190° C. to 220° C. have been observed with samples which are believed to be pure. The differences in hydrogen bonding could give rise to differences in the packing of the molecules in the crystal lattice, which in turn could result in different melting points. Samples of compound no 1 have been examined by the technique of differential scanning calorimetry, which seems to indicate the existence of a lower and higher melting form, the lower melting form being transformed to the higher melting form on heating. The melting point for any particular sample may depend upon the rate of heating. The two forms of compound 1 have been compared for herbicidal activity in greenhouse tests. Within the limits of accuracy of a biological experiment of this kind, the two forms showed no difference in herbicidal effect.

The compounds of the invention may be prepared by methods known in themselves, although it is believed that these methods have not previously been applied to make the compounds of the present invention. Thus, compounds wherein $R^6$ is hydrogen may be prepared by the method outlined in Scheme A.

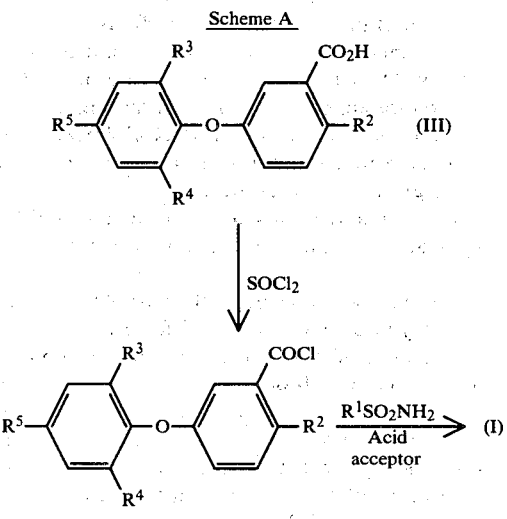

In Scheme A, an appropriately substituted carboxylic acid (III) is converted into the corresponding acid chloride (IV) by treatment with at least one molar proportion of thionyl chloride or another chlorinating agent, for example phosphorus oxychloride or phosphorus pentachloride, according to conventional procedures. The acid chloride (IV) so obtained is then treated with an alkane sulphonamide of formula $R^1SO_2NH_2$ in the presence of an acid acceptor to obtain the compounds of the invention (I). The sulphonamides $R^1SO_2NH_2$ are known or may be prepared by conventional methods.

The acid acceptor may be a tertiary amine, for example dimethylaniline or pyridine. The reaction may be carried out in the temperature range from ambient temperatures to elevated temperatures, for example from 25° C. up to 150° C. The products (I) may be isolated by conventional methods.

The carboxylic acids (III) required for Scheme A are in a number of cases known; compounds not already described in the literature may, however, by prepared by the methods described for the known compounds.

Compounds wherein the group $R^5$ is a trifluoromethyl group, $R^3$ is hydrogen, chlorine, or cyano, and $R^4$ is hydrogen for example, may be prepared by reacting at an elevated temperature a trifluoromethyl benzene substituted in the 4-position with a chlorine or fluorine atom, (a) with meta-hydroxybenzoic acid in the presence of an alkaline agent, for example sodium or potassium carbonate or (b) with the di-sodium or di-potassium salt of meta-hydroxy benzoic acid. When this approach is used, the $R^2$ substituent required in the end-product (in the cases where $R^2$ is not hydrogen) may conveniently be introduced by halogenation or nitration of the diphenyl ether so obtained as illustrated in Examples 5 and 7. The reaction of the meta-hydroxy benzoic acid and the 4-chloro or fluoro-substituted trifluoromethyl benzene is generally carried out at a temperature of from about 100° C. to 180° C. (although lower temperatures, e.g. from 50°–120° C. may sometimes be used) in a polar aprotic organic solvent, for example dimethyl sulphoxide, dimethyl formamide, sulpholane, N-methyl-2-pyrrolidone, hexamethylphosphoric triamide, and similar solvents. The nitration of the diphenyl ether so obtained may be carried out in a conventional way, for example by using a nitrating agent such as nitric acid/sulphuric acid, or potassium nitrate/sulphuric acid, optionally with a solvent such as ethylene dichloride, methylene dichloride, chloroform or perchloroethylene.

In a second approach for preparing the carboxylic acids (III), an ester, for example the methyl ester, of 5-chloro-2-nitrobenzoic acid or 5-fluoro-2-nitrobenzoic acid is reacted with a phenol of formula:

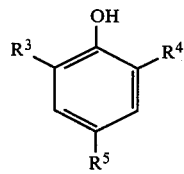

in the presence of a base such as sodium or potassium hydroxide or carbonate, or the like. The reaction may be carried out at a temperature of from 50° to 180° C. for example from 100° C. to 180° C. in a dipolar aprotic solvent selected from those mentioned above. This approach provides compounds of formula (III) in which the carboxy group is esterified. The ester group may be hydrolysed by standard procedures for example by treatment with alkali or acid to give compounds of formula (III) as illustrated in Example 8. This approach necessarily provides compounds (III) in which $R^2$ is a nitro group. If desired, the nitro group may be reduced by standard procedures to an amino group, diazotised, and converted into a halogen substituent. Example 10 describes the preparation of a 2-bromo compound of formula III.

Similarly, the 2-iodo compound 30 was prepared by reducing the corresponding 2-nitro compound (i.e. compound no 1 of Table I) to the 2-amino derivative with titanium trichloride. The 2-amino derivative was dissolved in dilute sodium hydroxide containing sodium nitrite and added to aqueous fluoroboric acid to give the corresponding diazonium salt. This was filtered off as its fluoborate salt. The fluoborate was dissolved in acetone and treated with sodium iodide in acetone to give the 2-iodo compound no 30.

The 2-fluoro compound 33 was obtained by a similar procedure starting with ethyl 5-(2-chloro-4-trifluoromethylphenoxy)-2-nitrobenzoate. This was reduced to the corresponding 2-amino compound with titanium trichloride, the 2-amino compound diazotised, and the diazonium salt isolated as its fluoborate. The diazonium fluoborate was heated to give ethyl 5-(2-chloro-4-trifluoromethylphenoxy)-2-fluorobenzoate. This was hydrolysed to the corresponding benzoic acid with sodium hydroxide solution at room temperature, and the benzoic acid converted to its acid chloride and reacted with methanesulphonamide to give compound no 33 in the usual way.

A third approach to preparing the carboxylic acids (III) is to react a substituted 4-chloro-nitrobenzene with meta-hydroxy benzoic acid in the presence of a base as described in the first approach above. Thus reaction of 3,4-dichloronitrobenzene with meta-hydroxy benzoic acid gives 3-(2-chloro-4-nitrophenoxy)benzoic acid. The nitro group in this compound can then be reduced to an amino group by a conventional procedure, diazotised, and converted to a bromine or chlorine atom, as illustrated in Example 9.

Another method of preparing the carboxylic acids (III) wherein one or both of the groups $R^3$ and $R^4$ are halogen atoms and $R^5$ is a $CF_3$ group comprises reacting a 2-amino-4-trifluoromethyl-6-(hydrogen or halogen)-substituted phenol (XI) with a 5-fluoro or chloro-2-nitrobenzoic acid ester as shown below:

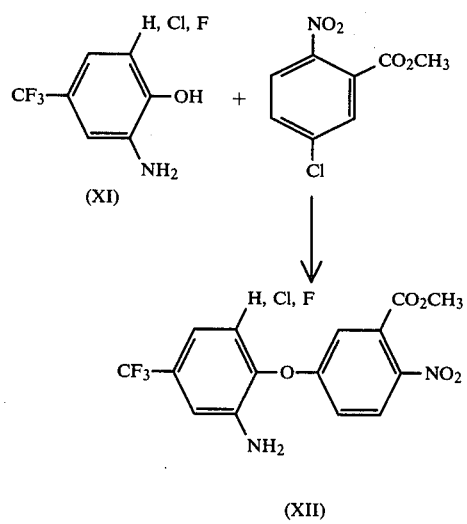

The reaction may be carried out using methyl ethyl ketone as a solvent and with anhydrous potassium carbonate as base. The reaction may be accelerated by heating. The amino group in the derivative (XII) may be diazotised and converted into a fluorine, chlorine, bromine or iodine substituent by conventional procedures. The compound so obtained may then be hydrolysed to the corresponding carboxylic acid and then converted to a compound of the invention by the process of Scheme A.

The 2-amino-4-trifluoromethylphenols (XI) required for the reaction sequence just described may be prepared by conventional methods. Thus, 2-amino-6-fluoro-4-trifluoromethylphenol may be prepared from 2-nitro-4-trifluoromethylchlorobenzene by reacting the latter with sodium methoxide to give 2-nitro-4-trifluoromethylanisole, and reducing this compound to 2-amino-4-trifluoromethylanisole. The latter compound may be diazotised and converted to its fluoborate salt and heated to give 2-fluoro-4-trifluoromethylanisole. This may then be nitrated to form 2-fluoro-6-nitro-4-trifluoromethylanisole, which is then reduced to give 2-amino-6-fluoro-4-trifluoromethylanisole. Finally the latter compound is heated with a demethylating agent, for example an excess of pyridine hydrochloride to give 2-amino-6-fluoro-4-trifluoromethylphenol.

By way of a further example, 2-amino-6-chloro-4-trifluoromethylphenol may be prepared from 3,4-dichlorobenzotrifluoride by nitrating the latter compound to give 5-nitro-3,4-dichlorobenzotrifluoride. This may then be reacted with sodium methoxide to give 2-chloro-6-nitro-4-trifluoromethylanisole. This may be treated with a demethylating agent (e.g. pyridine hydrochloride) to give 2-chloro-6-nitro-4-trifluoromethylphenol. Reduction of the latter compound (for example with sodium dithionite) gives the required 2-amino-6-chloro-4-trifluoromethylphenol.

An alternative method for preparing compounds of the invention in which $R^2$ is a nitro group is outlined in Scheme B.

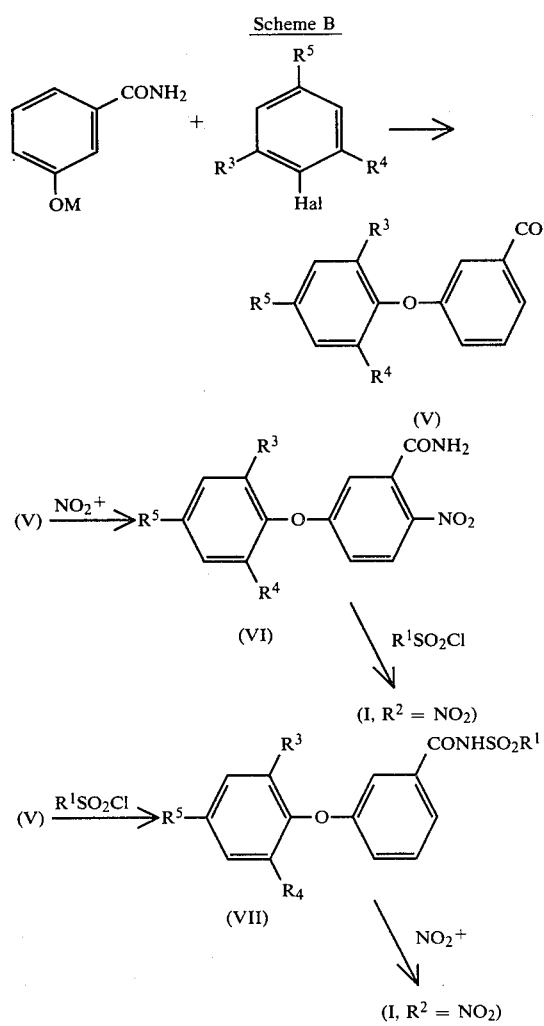

In Scheme B, the symbols $R^1$ to $R^5$ inclusive have the meanings previously assigned to them. The symbol M represents a metal, for example an alkali metal, for example sodium or potassium. The symbol Hal stands for halogen, for example fluorine, chlorine or bromine.

According to Scheme B, a metal salt of meta hydroxy benzamide is reacted with a suitably substituted halobenzene to give the diphenyl ether (V). The reaction may be carried out in a solvent or diluent which is inert towards the reactants and may be accelerated by the application of heat. The diphenyl ether (V) may then be converted to the compounds of the invention (I) by one or other of the two alternatives shown in Scheme B. In the first alternative, the diphenyl ether (V) is treated with a nitrating agent, denoted by the symbol $NO_2^+$ in Scheme B. The nitro compound (VI) so obtained is then treated with an alkane sulphonyl chloride $R^1SO_2Cl$ in the presence of an acid acceptor, for example pyridine, to give the compound of the invention (I, $R^1=NO_2$).

In the second alternative shown in Scheme B the steps shown in the first alternative are reversed. Thus the diphenyl ether (V) is first treated with an alkane sulphonyl chloride $R^1SO_2Cl$ in the presence of an acid acceptor, and the product (VII) so obtained is then treated with a nitrating agent to give the compound of the invention (I, $R^2=NO_2$).

A further scheme for preparing compounds of the invention in which $R^2$ is a nitro group is shown in Scheme C below:

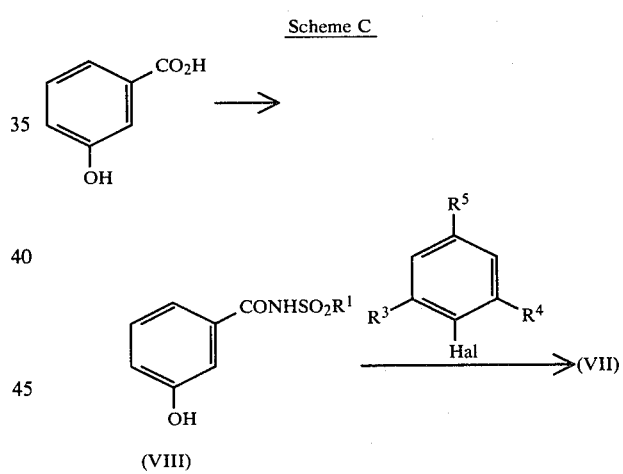

In Scheme C, metahydroxybenzoic acid is converted to the amide derivative (VIII). This may be done by converting the acid into meta hydroxy benzoyl chloride by standard methods, and reacting the meta hydroxy benzoyl chloride with the appropriate alkane sulphonamide $R^1SO_2NH_2$ in the presence of an acid acceptor, for example pyridine. Alternatively the meta hydroxybenzoic acid may be converted to meta hydroxybenzamide by standard methods, and the meta hydroxybenzamide then reacted with the appropriate alkanesulphonyl chloride $R^1SO_2Cl$ in the presence of an acid acceptor for example pyridine. The amide derivative (VIII) prepared by either method is then reacted in the form of its metal salt, for example its sodium or potassium phenolate salt, with the appropriately substituted halobenzene to give the diphenyl ether derivative (VII). This may then be converted by nitration, as in Scheme B, to the compound of the invention (I, $R^2=NO_2$).

A yet further scheme for preparing compounds of the invention in which $R^2$ is a nitro group is outlined in Scheme D below:

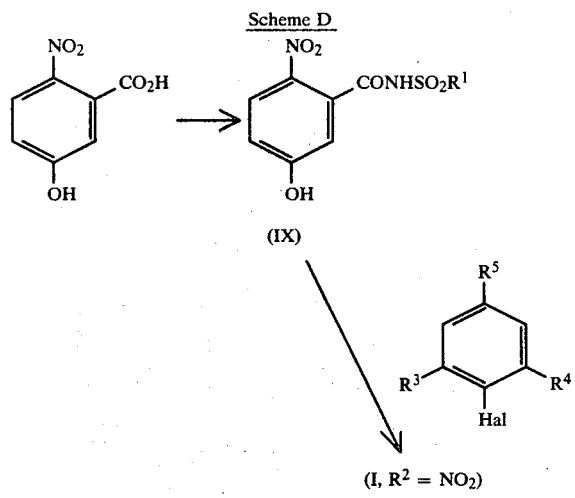

In Scheme D, 3-hydroxy-6-nitrobenzoic acid is converted to the amide derivative (IX). This may be done by converting the acid into the corresponding acid chloride by standard methods. The acid chloride is then reacted with the appropriate alkane sulphonamide $R^1SO_2NH_2$ in the presence of an acid acceptor (e.g. pyridine) to give the amide derivative (IX). Alternatively, the 3-hydroxy-6-nitrobenzoic acid may be converted to 3-hydroxy-6-nitrobenzamide by standard methods, and the benzamide then reacted with the appropriate alkanesulphonyl chloride $R^1SO_2Cl$ in the presence of an acid acceptor (e.g. pyridine) to give the amide derivative (IX). The amide derivative (IX) obtained by either route may then, in the form of its phenolate salt with an alkali metal (e.g. sodium or potassium) be reacted with an appropriately substituted halobenzene to give the compound of the invention (I, $R = NO_2$). The reaction with the halobenzene may be carried out in a solvent or diluent inert to the reactants and may be accelerated by the application of heat.

A yet further scheme for preparing compounds of the invention in which $R^2$ is a nitro group is outlined in Scheme E below:

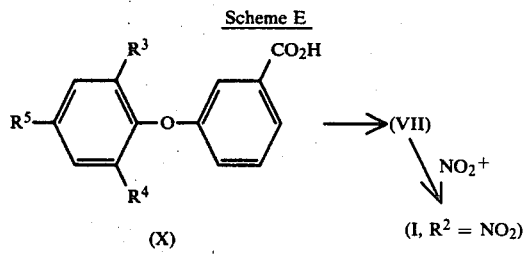

In Scheme E the carboxylic acid (X) is converted to the amide derivative of formula (VII) shown in Scheme B. This may then be nitrated as shown in Scheme B to give the required compound. The conversion of the acid (X) to the amide derivative (VII) may be done by converting the carboxylic acid to the corresponding acid chloride by standard methods and then reacting this acid chloride with the appropriate alkanesulphonamide $R^1SO_2NH_2$ in the presence of an acid acceptor to obtain the amide derivative (VII). Alternatively the carboxylic acid (X) may be converted to the corresponding carboxylic acid amide by standard methods and the amide then reacted with the appropriate alkanesulphonyl chloride $R^1SO_2Cl$ in the presence of an acid acceptor to give the amide derivative (VII).

Schemes B to E above relate to compounds to which $R^2$ is a nitro group. However, it will be obvious that these schemes may readily be adapted to prepare compounds in which $R^2$ is halogen.

Compounds of the invention wherein $R^6$ is an alkyl group may be prepared from the corresponding compounds wherein the group $R^6$ is a hydrogen atom, by reaction with diazo-alkane. Thus where $R^6$ is a methyl group, the corresponding compound wherein $R^6$ is hydrogen may be reacted with diazomethane and the corresponding compound wherein $R^6$ is methyl recovered. The procedures for carrying out such methylation reactions are well known to those skilled in the art.

The compounds of the invention are useful both as pre- and post-emergence herbicides. Pre-emergence herbicides are usually used to treat the soil in which a crop is to be planted, by application before or during seeding, or after seeding and before the crop emerges. Post-emergence herbicides are applied after the crop plants have emerged from the soil. Compounds of the invention may be used as selective herbicides in a variety of crops, including for example cotton, soya bean, peas, wheat, barley and rice. Compounds of the invention may also be used a total herbicides. The compounds of the invention may be applied by any of the conventional techniques for applying herbicides. When applied as pre-emergence herbicides they may for example be sprayed on the surface of the soil before or during seeding, or after seeding and before emergence of the crop. In some situations for example in pre-emergence application to soya bean crops it may be advantageous to incorporate the compound of the invention into the soil before planting the crop. This may be done by applying the compound to the surface of the soil and then discing or harrowing the soil to mix the compound with the soil. Alternatively use may be made of the applicators which have been developed for placing herbicides in a band beneath the surface of the soil.

In another aspect, therefore, the invention provides a process of killing or severely injuring unwanted plants, which comprises applying to the plants or to the locus thereof, a compound of the formula (I) or a salt thereof as hereinbefore defined.

As will be understood by those skilled in the art, the amount of the compound (I) applied will depend upon a variety of factors, for example the particular compound chosen for use and the identity of the unwanted plants. By way of general guidance, however, an amount of from 0.1 to 5.0 kilograms per hectare is usually suitable, while from 0.25 to 1.0 kilograms per hectare is preferred.

Particular examples of compounds which may be used as selective herbicides in crops of cotton include compounds 1, 2, 7, 9 and 17 of Table I.

Particular examples of compounds which maybe used as selective herbicides in crops of rice include compounds 7, 8, 9 and 17 of Table I.

Particular examples of compounds which may be used as selective herbicides in crops of soya bean include compounds 1 to 6, 16 to 18, and 21 to 24 of Table I. Preferably the compound is applied at a rate of 0.1 to 1.5 kilograms per hectare to the area of the soya bean crop. The compound may be applied before or after the emergence of the crop. The compounds of the invention have the advantage that they are capable of controlling Cyperus rotundus and maize. Maize may appear as a weed in crops of soya grown on land which has previously been used for maize.

The compounds used in the process of the invention are preferably applied in the form of a composition, in which the active ingredient is mixed with a carrier comprising a solid or liquid diluent. In another aspect, therefore, the invention provides a herbicidal composition, comprising as an active ingredient a compound of the formula (I) as hereinbefore defined, in admixture with a solid or liquid diluent. Preferably the composition also comprises a surface-active agent.

The solid compositions of the invention may be for example, in the form of dusting powders, or may take the form of granules. Suitable solid diluents include, for example, kaolin, bentonite, kieselguhr, dolomite, calcium carbonate, talc, powdered magnesia, and Fuller's earth. Solid compositions also include soluble powders and granules which may comprise a salt of a compound of the invention in admixture with a water-soluble carrier, or a mixture of a compound of the invention wherein $R^6$ is hydrogen with an alkali for example sodium or potassium carbonate; when mixed with water the composition gives a solution of a salt of the compound of the invention.

Solid compositions may also be in the form of dispersible powders or grains comprising in addition to the active ingredient, a wetting agent to facilitate the dispersion of the powder or grains in liquids. Such powders or grains may include fillers, suspending agents and the like.

Liquid compositions include aqueous solutions, dispersions and emulsions containing the active ingredient preferably in the presence of one or more surface active agents. Water or organic liquids may be used to prepare solutions, dispersions, or emulsions of the active ingredient. The liquid compositions of the invention may also contain one or more corrosion inhibitors for example lauryl isoquinolinium bromide.

Surface active agents may be of the cationic, anionic or non-ionic type. Suitable agents of the cationic type include for example quaternary ammonium compounds, for example cetyltrimethyl ammonium bromide. Suitable agents of the anionic type include for example soaps, salts of aliphatic mono-esters of sulphuric acid, for example sodium lauryl sulphate; and salts of sulphonated aromatic compounds, for example dodecylbenzenesulphonate, sodium, calcium and ammonium lignosulphonate, butylnaphthalene sulphonate, and a mixture of the sodium salts of diisopropyl- and triisopropylnaphthalenesulphonic acid. Suitable agents of the non-ionic type include, for example, the condensation products of ethylene oxide with fatty alcohols such as oleyl alcohol and cetyl alcohol, or with alkyl phenols such as octyl-phenol, nonylphenol, and octylcresol. Other non-ionic agents are the partial esters derived from long chain fatty acids and hexitol anhydrides, for example sorbitol monolaurate; the condensation products of the said partial esters with ethylene oxide and the lecithins.

The compositions which are to be used in the form of aqueous solutions, dispersions or emulsions are generally supplied in the form of a concentrate containing a high proportion of the active ingredient, the concentrate being diluted with water before use. These concentrates are usually required to withstand storage for prolonged periods and after such storage to be capable of dilution with water in order to form aqueous preparations which remain homogeneous for a sufficient time to enable them to be applied by conventional spray equipment.

The compositions of the invention may contain, in addition to carriers and surface-active agents, various other constituents to increase their usefulness. They may contain, for example, buffering salts to maintain the pH of the composition within a desired range; antifreeze agents, for example urea or propylene glycol; adjuvants, for example oils and humectants; and sequestrants, for example citric acid and ethylenediaminetetracetic acid, which help to prevent the formation of insoluble precipitates when the compositions are diluted with hard water. Aqueous dispersions may contain anti-settling agents and anti-caking agents. The compositions may in general contain a dye or pigment to impart a characteristic colour. Agents for increasing viscosity may be added to reduce the formation of fine droplets during spraying, and thereby reduce spray drift. Other additives useful for particular purposes will be known to those skilled in the formulation art.

In general concentrates may conveniently contain from 10 to 85% and preferably from 25 to 60% by weight of active ingredient. Dilute preparations ready for use may contain varying amounts of the active ingredient, depending upon the purpose for which they are to be used; however, dilute preparations suitable for many uses contain between 0.01% and 10% and preferably between 0.1% and 1% by weight of the active ingredient.

The invention is illustrated by the following Examples, in which all parts are by weight and all temperatures in degrees Centigrade unless otherwise stated.

EXAMPLE 1

This Example illustrates the preparation of compound No. 1 of Table 1.

5(2-chloro-4-trifluoromethylphenoxy)-2-nitrobenzoic acid (1.58 g) was heated under reflux in an excess of thionyl chloride (20 ml) for 90 minutes. The excess of thionyl chloride was removed in a vacuum and the remaining oil taken up in dry pyridine (20 ml). Methanesulphonamide (0.45 g) was added and the mixture stirred at room temperature overnight. The pyridine was removed in a vacuum and the remaining oil mixed with 2-molar hydrochloric acid and extracted with ether (2 × 100 ml). The ether extracts were washed with water (100 ml), dried, and evaporated in a vacuum. The residual solid was recrystallised from isopropanol to give 5-(2-chloro-4-trifluoromethylphenoxy)-2-nitro-N-methanesulphonyl benzamide (Compound no 1) with a melting point of 201° C. In a similar way, but using the appropriate carboxysubstituted diphenyl ether and the appropriate sulphonamide in place of methanesulphonamide, the compounds listed in Table 1 were prepared, except for compounds 6, 8 and 10, whose preparation is described in Example 3.

EXAMPLE 2

This Example illustrates a method of preparing compound No. 1 of Table 1 alternative to that described in Example 1.

3-(2-Chloro-4-trifluoromethylphenoxy)benzoic acid (20.5 g) was taken up in thionyl chloride (50 ml) and heated under reflux for 2 hours. The excess of thionyl chloride was removed under reduced pressure. The acid chloride which remained was stirred and cooled in ice and salt while dry, cooled pyridine (50 ml) was added. After 5 minutes, methanesulphonamide (6.4 g) was added. When it had dissolved, the ice and salt bath was removed and the mixture was left at room temperature overnight. The pyridine was then removed under reduced pressure. The residue was washed with water and dissolved in ethyl acetate. The solution was washed with 2-molar hydrochloric acid, then with water, dried, and evaporated. The residue (22 g) was recrystallised from a mixture of ethyl acetate and petroleum ether (b.p. 60°–80°) giving 3-(2-chloro-4-trifluoromethyl)-N-methanesulphonyl benzamide with a melting point of 173°–174°.

The benzamide derivative so prepared (1.6 g) was added to a mixture of concentrated sulphuric acid (6.4 ml) and dichloroethane (4 ml) which was stirred and kept at 0° C. in an ice and salt bath. After 5 minutes, potassium nitrate (0.51 g) was added in portions over a period of 15 minutes. The mixture was stirred for a further 45 minutes at 0° C. and then stored at −18° C. overnight. The mixture was poured into ice and water (60 ml) and then extracted with ethyl acetate. The ethyl acetate extract was washed with water, dried, and evaporated. The residue was crystallised twice from a mixture of ethyl acetate and petroleum ether (b.p. 60°–80°) and gave compound 1 (1.0 g) identified by its melting point and spectral properties with the compound made in Example 1.

EXAMPLE 3

This Example illustrates the preparation of compounds Nos. 6, 8 and 10 of Table 1. Compound No. 1 (1.8 g) in diethyl ether (50 ml) containing a little methanol was cooled to 0° C. while a solution of diazomethane in ether was added until the yellow colour of the solution did not disappear after addition. The solution was left overnight at room temperature and a drop of glacial acetic acid was added to destroy excess of diazomethane. The solvent was removed and the remaining oil taken up in ethyl acetate and the solution washed with sodium bicarbonate solution and then with water, dried and evaporated to yield an oil. This was extracted with boiling petroleum (b.p. 60°–80° C.) The cooled extracts deposited an oil. This was dissolved in the minimum of diethyl ether and left to stand. The white solid which separated was collected and dried to give compound no 6 (0.5 g). Compounds 8 and 10 were prepared in a similar way, using diazomethane and compounds nos 7 and 9 respectively as starting materials.

EXAMPLE 4

This Example illustrates the preparation of 2-chloro-5(2-chloro-4-trifluoromethylphenoxy)benzoic acid.

A solution of 3(2-chloro-4-trifluoromethylphenoxy)-benzoic acid (5 g) in glacial acetic acid (30 ml) was heated under reflux while chlorine was passed through the solution for 5 hours. The solution was left to stand for two days at room temperature and then poured into cold water (500 ml). An off-white gummy solid separated. This was extracted with ethyl acetate and the extract dried and evaporated. The brown oil remaining was dissolved in sodium bicarbonate solution and the solution extracted with ethyl acetate. The aqueous solution was acidified with hydrochloric acid. The solution was decanted from the precipitated gum, and the gum taken up in boiling hexane. The hexane solution was filtered and allowed to cool. The required 2-chloro-5(2-chloro-4-trifluoromethylphenoxy)benzoic acid was obtained (1.0 g) as crystals of melting point 103°–104°. This acid was used as starting material for compounds 7 and 8.

EXAMPLE 5

This Example illustrates the preparation of 2-bromo-5(2-chloro-4-trifluoromethylphenoxy)benzoic acid.

Methyl 3(-chloro-4-trifluoromethylphenoxy)benzoate (10 g) was heated under reflux in glacial acetic acid (50 ml) while bromine (19.4 g) was added dropwise over a period of 1 hour. The mixture was heated under reflux for a further 4 hours, and further bromine (20 g) added. The mixture was heated for a further 8 hours under reflux. The acetic acid and excess of bromine were evaporated off and the residue taken up in water and brought to pH7 with sodium bicarbonate. The solution was extracted with ether and then acidified. The gummy white solid which separated was extracted with dichloromethane. The dichloromethane solution was dried and evaporated to give a white solid. This was identified as 2-bromo-5(2-chloro-4-trifluoromethylphenoxy)benzoic acid. This acid (8 g) was heated under reflux for 2½ hours in thionyl chloride (80 ml) and the excess of thionyl chloride then removed. The residue was treated at 10° C. with a solution of sodium (0.6 g) dissolved in methanol (40 ml) and then heated under reflux for 1 hour. The solvent was removed and the residue shaken with water and ether. Distillation of the ether solution gave the required methyl ester (5.2 g) with a boiling range of 152°–154°/0.1 Torr. Alkaline hydrolysis of this ester gave the carboxylic acid required as starting material for the preparation of compounds 9 and 10 of Table 1.

EXAMPLE 6

This Example illustrates the preparation of 3(4-trifluoromethylphenoxy)benzoic acid.

3-Hydroxybenzoic acid (6.9 g) was added in portions to potassium hydroxide (6.9 g) in solution in dry methanol (30 ml), with stirring. When addition was complete, the mixture was left for 15 minutes at room temperature and then the solvent removed under reduced pressure. The residue was dissolved in dimethylsulphoxide (30 ml) and anhydrous potassium carbonate (2.5 g) was added, followed by p-chlorobenzotrifluoride (9.03 g) in dimethyl sulphoxide (10 ml) dropwise, with stirring. The mixture was stirred and heated at 115° C. for 20 hours, then cooled and poured into water. The mixture was extracted twice with ethyl acetate and the aqueous solution then brought to pH2 with concentrated hydrochloric acid. The solid which separated was dried and washed with petroleum (b.p. 40°–60° C.) and recrystallised from a mixture of toluene and petroleum to give 6.6 g of the required 3-(4-trifluoromethylphenoxy)benzoic acid having a melting point of 140°–142° C., which was used as a starting material for compound No. 14 of Table 1.

EXAMPLE 7

This Example illustrates the preparation of 5-(2-cyano-4-trifluoromethylphenoxy)benzoic acid, used as the starting material for compound No. 15 of Table 1, and of 2-nitro-5-(2-cyano-4-trifluoromethylphenoxy)-benzoic acid, useful as the starting material for compound 16.

(a) Preparation of 3-(2-cyano-4-trifluoromethylphenoxy)benzoic acid

3-Hydroxybenzoic acid (27.6 g), 4-chloro-3-cyano-benzotrifluoride (41.1 g) and anhydrous potassium carbonate (55.2 g) were stirred together for 7½ hours at 100° C. in dry dimethylformamide (500 ml) and then left at room temperature for 65 hours. The solvent was then removed under reduced pressure and the residue taken up in water and acidified with dilute hydrochloric acid. The solid which separated was washed with water, dissolved in ether and the solution dried and concentrated. The colourless solid which separated was recrystallised to give the benzoic acid derivative (24.0 g) with a melting point of 224°–226° C.

(b) Preparation of 5-(2-cyano-4-trifluoromethylphenoxy)-2-nitrobenzoic acid

The product from (a) (9.22 g) was added in portions to a mixture of 1,2-dichloroethane (25 ml) and concentrated sulphuric acid (40 ml) stirred at 0° C. Potassium nitrate (3.13 g) was then added in portions with stirring at 0° C., over a period of 15 minutes. The mixture was then stirred at 0° C. for 30 minutes, allowed to warm to room temperature, and poured into 200 ml of ice and water. The mixture was stirred until the ice had melted, and filtered with suction. The solid which separated on evaporation of the dichloroethane was washed with water and taken up in ether. The ether solution was treated with charcoal, dried and petroleum (b.p. 40°–60° C.) added. The solid which separated was identified as the required benzoic acid derivative (7.8 g) having a melting point of 190°–192° C.

EXAMPLE 8

This Example illustrates the preparation of 5-(2,4-dichlorophenoxy)-2-nitrobenzoic acid, useful as the starting material for the preparation of compound No. 17 of Table 1.

The known compound methyl 2-nitro-5-(2,4-dichlorophenoxy)benzoate (55.0 g) was heated under reflux with 2 molar sodium hydroxide solution for 4 hours. The clear solution was cooled and acidified with hydrochloric acid. A yellow gum separated, which crystallised on stirring. The solid was recrystallised from toluene to give the required benzoic acid derivative (30.2 g), with a melting point of 167.5°–169.5° C.

EXAMPLE 9

This Example illustrates the preparation of 3(2,4-dichlorophenoxy)benzoic acid.

(a) Preparation of 3(2-chloro-4-nitrophenoxy)benzoic acid

A mixture of 3-hydroxybenzoic acid (5 g), dimethyl formamide (50 ml), 3,4-dichloronitrobenzene (7 g) and anhydrous potassium carbonate (10 g) was stirred and heated at 100° C. for 14 hours. The solvent was removed under reduced pressure and the residue poured into water and acidified with 2 molar hydrochloric acid. The yellow solid which separated was recrystallised from toluene to give the required benzoic acid derivative (8.0 g) with a melting point of 172°–173° C.

(b) Concentrated hydrochloric acid (200 ml) was added dropwise to a mixture of 3(2-chloro-4-nitrophenoxy)benzoic acid (20 g) and granulated tin (40 g), the temperature being kept at 10°–15° C. When addition was complete, the mixture heated at 60° C. for 45 minutes, ethanol (100 ml) added, and the heating continued for another two hours. The mixture was allowed to cool, and the solid which separated was collected, dried, and extracted with hot methanol. Evaporation of the methanol extract gave the hydrochloride of 3(4-amino-2-chlorophenoxy)benzoic acid (19.5 g), with a melting point of 228°–232° C. (decomp).

(c) The product (10 g) from paragraph (a) was dissolved in dimethyl formamide (150 ml), cooled to 5°–10° C. and concentrated hydrochloric acid (40 ml) added dropwise, the temperature being kept at 10°–15° C. The mixture was then kept at 5° C. while sodium nitrite (5.2 g) in water (20 ml) was added dropwise with stirring over a period of 30 minutes. The solution so prepared was added dropwise to a solution of cuprous chloride (19 g) in concentrated hydrochloric acid (150 ml) kept at 10° C., giving a thick green suspension. When addition was complete, the mixture was left to stand overnight and then heated to 60° C. for 30 minutes. The white solid was filtered off, dried, and recrystallised from petroleum (100°–120° C.) to give 3(2,4-dichlorophenoxy)benzoic acid (5.1 g) with a melting point of 143°–144° C. This compound was used as starting material for compound No. 19 of Table 1.

EXAMPLE 10

This Example illustrates the preparation of 2-bromo-5-(2,4-dichlorophenoxy)benzoic acid useful as a starting material for compound No. 20 of Table 1.

(a) Preparation of 2-amino-5-(2,4-dichlorophenoxy)benzoic acid hydrochloride Concentrated hydrochloric acid (100 ml) was added dropwise to a mixture of 5-(2,4-dichlorophenoxy)-2-nitrobenzoic acid (10 g) and granulated tin (20 g) cooled to 10°–15° C. The mixture was then heated to 60°–70° C. for 1 hour. Ethanol (100 ml) was added and the mixture heated for a further 2 hours at 60°–70° C. The precipitate was collected and recrystallised from ethanol to give the hydrochloride (3.8 g) with a melting point of 166°–168° C. with decomposition.

(b) Preparation of 2-bromo-5-(2,4-dichlorophenoxy)benzoic acid

The product from (a) above (3.8 g) dissolved in dimethyl formamide (100 ml) was cooled to 5° C. and concentrated hydrochloric acid (50 ml) added. The solution was kept at 5°–10° C. while sodium nitrite (2.0 g) in water (10 ml) was added dropwise with stirring. The solution so prepared was added dropwise to boiling hyrobromic acid (48%; 75 ml) containing cuprous bromide (7 g). When addition was complete the reaction was heated for another 15 minutes and then allowed to cool to room temperature. The mixture was diluted with water and extracted with ether. The ether extracts yielded an oil which solidified on standing and was recrystallised from petroleum (b.p. 100°–120° C.) to give the bromo-acid (1.0 g) with a melting point of 132°–133° C.

EXAMPLE 11

This Example illustrates the preparation of compound No. 21 of Table 1.

(a) Preparation of ethyl 2-nitro-5-(2,4,6-trichlorophenoxy)benzoate 2,4,6-Trichlorophenol (12.0 g) and anhydrous potassium carbonate (44 g) in dimethyl formamide (60 ml) were heated under reflux for 90 minutes and then left to cool overnight. Half of the dimethyl formamide was then distilled off. The remaining solution was cooled to 150°–160° C. and ethyl 5-chloro-2-nitrobenzoate (13.3 g) was added. The mixture was then heated under reflux for 8 hours. The dimethyl formamide was then removed under reduced pressure and the residue shaken with water (250 ml) and ether (250 ml). The ether layer was evaporated and washed with water and then dried and evaporated. The remaining oil was distilled and the fraction (9.9 g) boiling at 190°/0.1 Torr was collected and identified as the required ester.

(b) Preparation of 2-nitro-5-(2,4,6-trichlorophenoxy)benzoic acid

The product from paragraph (a) (6.86 g) in ethanol (50 ml) was heated and stirred with a solution of sodium hydroxide (0.8 g) in water (10 ml) at 60°–70° C. for 4 hours. The mixture was then cooled and the ethanol removed under reduced pressure. The residue was diluted to 100 ml with water and brought to pH 2 with concentrated hydrochloric acid. The solid which separated was collected and recrystallised from toluene to give the required benzoic acid derivative (4.26 g) with a melting point of 192°–192.5° C.

(c) Preparation of compound No. 21

The product from (b) above (1.5 g) was heated to reflux in thionyl chloride (10 ml) for 9 hours and the excess of thionyl chloride then removed under reduced pressure. The residue was taken up in pyridine (20 ml) and stirred with methanesulphonamide (0.7 g) for 7 hours and the solution then left to stand for two days. The pyridine was then removed under reduced pressure. The oil which remained was mixed with 2 molar hydrochloric acid (50 ml) and the solution extracted with ether (100 ml). The ether solution was washed with water (100 ml) and then dried and evaporated to give a solid which was recrystallised from toluene, to give 2-nitro-5-(2,4,6-trichlorophenoxy)-N-methanesulphonylbenzamide (1.05 g) with a melting point of 227.5° C.

EXAMPLE 12

This Example ilustrates the preparation of 2-nitro-5-(2,4,6-tribromophenoxy)benzoic acid, useful as starting material for the preparation of compound No. 22 of Table 1.

(a) Preparation of ethyl 2-nitro-5-(2,4-tribromophenoxy)benzoate

Ethyl 5-chloro-2-nitrobenzoate (10 g) and 2,4,6-tribromophenol (14.6 g) were heated and stirred with sodium carbonate (6.1 g) in dimethyl formamide at 130° C. for 17 hours. A further quantity of sodium carbonate (6.1 g) was then added and the mixture heated under reflux for another 38 hours. The solvent was removed under reduced pressure and the residue shaken with water and dichloromethane. The dichloromethane was dried and evaporated and the residue taken up in ether and the ether solution washed with water. The ether solution was dried and evaporated to leave an oil. This was distilled and the fraction (2.14 g) boiling at 202°–210° C./0.1 Torr collected.

(b) Preparation of 2-nitro-5-(2,4,6-tribromophenoxy)benzoic acid

The ester from (a) above (4.9 g) was stirred in ethanol (50 ml) with sodium hydroxide (0.4 g) dissolved in water (5 ml) at 60°–70° C. for 4 hours. The solvent was then removed under reduced pressure and the residue taken up in water and heated and stirred at 60° C. for five minutes. The solution was cooled and brought to pH 2 with hydrochloric acid and extracted with ether (200 ml). The ether extracts yielded an oil which was dissolved in sodium carbonate solution and the solution extracted with dichloromethane. The aqueous solution was then acidified and extracted with ether. The ether extracts yielded an oil which was recrystallised from a mixture of toluene and petroleum, to give the acid (1.86 g) with a melting point of 162°–169.5° C.

EXAMPLE 13

This Example illustrates the herbicidal properties of compounds of Table 1. The compounds were submitted to herbicide tests as described below.

Each compound was formulated for test by mixing an appropriate amount of it with 5 ml of an emulsion prepared by diluting 160 ml of a solution containing 21.8 grams per liter of Span 80 and 78.2 grams per liter of Tween 20 in methylcyclohexanone to 500 ml with water. Span 80 is a Trade Mark for a surface-active agent comprising sorbitan monolaurate. Tween 20 is a Trade Mark for a surface-active agent comprising a condensate of 20 molar proportions of ethylene oxide with sorbitan monolaurate. The mixture of the compound and the emulsion was then shaken with glass beads and diluted to 40 ml with water. The spray composition so prepared was sprayed on to young pot plants (post-emergence test) of the species named in Table 2 below, at a rate equivalent to 1000 liters per hectare. Damage to plants was assessed 14 days after spraying by comparison with untreated plants, on a scale of 0 to 5 where 0 is 0 to 20% damage and 5 is complete kill. In the table of results, a dash (—) means that no test was made.

A test was also carried out to detect post-emergence herbicidal activity. Seeds of the test species were placed on the surface of fibre trays of soil and were sprayed with the compositions at the rate of 1000 liters per hectare. The seeds were then covered with further soil. Three weeks after spraying, the seedlings in the spraying fibre trays were compared with the seedlings in unsprayed control trays, the damage being assessed on the same scale of 0 to 5.

The results of the tests are given in Table 2 below.

TABLE 2

| COMPOUND No. | RATE OF APPLICATION kg/ha | PRE- OR POST-EMERGENCE APPLICATION | TEST PLANTS | | | | | | | | | | | |
|---|---|---|---|---|---|---|---|---|---|---|---|---|---|---|
| | | | Sb | Rp | Ct | Sy | Mz | Ww | Rc | Sn | Ip | Am | Pi | Ca |
| 1 | 0.25 | Pre | 5 | 5 | 2 | 0 | 4 | 4 | 3 | 5 | 2 | 5 | 5 | 5 |
| | | Post | 5 | 5 | 4 | 1 | 4 | 3 | 3 | 5 | 5 | 5 | 5 | 5 |
| 1 | 1.0 | Pre | 5 | 5 | 3 | 1 | 5 | 4 | 4 | 5 | 5 | 5 | 5 | 5 |
| | | Post | 5 | 5 | 4 | 1 | 4 | 4 | 5 | 5 | — | 5 | 5 | 5 |

TABLE 2-continued

| | | | | | | | | | | | | | | |
|---|---|---|---|---|---|---|---|---|---|---|---|---|---|---|
| 1 | 5.0 | Pre | 5 | 5 | 4 | 0 | 5 | 5 | 5 | 5 | 5 | 5 | 5 | 5 |
| | | Post | 5 | 5 | 4 | 2 | 5 | 5 | 4 | 5 | — | 5 | 5 | 5 |
| 2 | 0.2 | Pre | 5 | 5 | 0 | 0 | 1 | 0 | 0 | 5 | 0 | 5 | 3 | 5 |
| | | Post | 1 | 4 | 1 | 0 | 1 | 2 | 0 | 5 | 4 | 5 | 3 | 4 |
| 2 | 1.0 | Pre | 5 | 5 | 0 | 1 | 4 | 4 | 2 | 5 | 0 | 5 | 5 | 5 |
| | | Post | 5 | 5 | 2 | 1 | 2 | 4 | 2 | 5 | 5 | 5 | 5 | 4 |
| 3 | 0.2 | Pre | 5 | 5 | 0 | 0 | 0 | 0 | 0 | 4 | 0 | 5 | 3 | 3 |
| | | Post | 2 | 4 | 1 | 0 | 0 | 0 | 0 | 5 | 4 | 3 | 1 | 4 |
| 3 | 1.0 | Pre | 5 | 5 | 1 | 0 | 0 | 0 | 0 | 5 | 0 | 5 | 5 | 5 |
| | | Post | 2 | 5 | 1 | 1 | 1 | 1 | 0 | 5 | 5 | 5 | 3 | 4 |
| 3 | 5.0 | Pre | 5 | 5 | 3 | 0 | 4 | 2 | 0 | 5 | 4 | 5 | 5 | 5 |
| 4 | 0.25 | Pre | 5 | 4 | 1 | 0 | 0 | 0 | 0 | 5 | 3 | 5 | 3 | 5 |
| | | Post | 4 | 5 | 4 | 1 | 2 | 0 | 0 | 5 | — | 5 | 3 | 5 |
| 4 | 1.0 | Pre | 5 | 5 | 2 | 1 | 1 | 1 | 0 | 5 | 4 | 5 | 5 | 5 |
| | | Post | 5 | 5 | 4 | 1 | 3 | 0 | 0 | 5 | — | 5 | 3 | 5 |
| 4 | 5.0 | Pre | 5 | 5 | 4 | 1 | 2 | 1 | 2 | 5 | 5 | 5 | 5 | 5 |
| | | Post | 5 | 5 | 4 | 2 | 3 | 0 | 2 | 5 | — | 5 | 4 | 5 |
| 5 | 0.2 | Pre | 1 | 0 | 0 | 0 | 0 | 0 | 0 | 2 | 0 | 3 | 0 | 3 |
| | | Post | 0 | 0 | 1 | 1 | 0 | 0 | 0 | 3 | 2 | 2 | 0 | 3 |
| 5 | 1.0 | Pre | 3 | 4 | 1 | 0 | 0 | 0 | 0 | 3 | 0 | 5 | 0 | 3 |
| | | Post | 1 | 2 | 1 | 2 | 0 | 0 | 0 | 5 | 3 | 4 | 1 | 4 |
| 5 | 5.0 | Pre | 5 | 5 | 2 | 1 | 1 | 0 | 0 | 4 | 4 | 5 | 5 | 5 |
| 6 | 0.2 | Pre | 1 | 3 | 0 | 0 | 1 | 1 | 0 | 4 | 0 | 5 | — | 4 |
| | | Post | 4 | 4 | 1 | 2 | — | 1 | 0 | 2 | 5 | 5 | 4 | 4 |
| 6 | 1.0 | Pre | 5 | 5 | 1 | 0 | 2 | 2 | 3 | 5 | 0 | 5 | — | 5 |
| | | Post | 4 | 5 | 2 | 2 | — | 2 | 1 | 5 | 5 | 5 | 5 | 4 |
| 6 | 5.0 | Post | 5 | 5 | 4 | 2 | 4 | 2 | 2 | 5 | 5 | 5 | 5 | 4 |
| 7 | 0.25 | Pre | 5 | 5 | 0 | 5 | 2 | 0 | 0 | 5 | 1 | 5 | 5 | 5 |
| | | Post | 5 | 5 | 3 | 2 | 3 | 1 | 0 | 5 | 4 | 5 | 4 | 5 |
| 7 | 1.0 | Pre | 5 | 5 | 1 | 5 | 5 | 4 | 0 | 5 | 3 | 5 | 5 | 5 |
| | | Post | 5 | 5 | 5 | 4 | 2 | 4 | 1 | 5 | 5 | 5 | 4 | 5 |
| 7 | 5.0 | Pre | 5 | 5 | 1 | 5 | 5 | 5 | 3 | 5 | 5 | 5 | 5 | 5 |
| | | Post | 5 | 5 | 4 | 4 | 4 | 4 | 3 | 5 | 5 | 5 | 4 | 5 |
| 8 | 0.2 | Pre | 1 | 0 | — | 0 | 0 | 0 | 0 | 2 | 0 | 3 | — | 0 |
| | | Post | 5 | 4 | 1 | 1 | 3 | 0 | 0 | 2 | 4 | 5 | 5 | 4 |
| 8 | 1.0 | Pre | 3 | 1 | 0 | 0 | 0 | 0 | 0 | 4 | 0 | 5 | — | 4 |
| | | Post | 5 | 5 | 2 | 1 | 3 | 1 | 0 | 4 | 4 | 5 | 5 | 4 |
| 8 | 5.0 | Pre | 5 | 4 | 1 | 2 | 0 | 2 | 0 | 5 | 3 | 5 | — | 5 |
| | | Post | 5 | 5 | 4 | 1 | 4 | 2 | 1 | 4 | 5 | 5 | 5 | 4 |
| 9 | 0.25 | Pre | 5 | 5 | 0 | 2 | 3 | 1 | 0 | 5 | 1 | 5 | 4 | 5 |
| | | Post | 3 | 5 | 2 | 3 | 3 | 2 | 0 | 5 | 4 | 5 | 4 | 5 |
| 9 | 1.0 | Pre | 5 | 5 | 1 | 5 | 5 | 4 | 0 | 5 | 5 | 5 | 5 | 5 |
| | | Post | 4 | 5 | 3 | 4 | 4 | 4 | 1 | 5 | 5 | 5 | 4 | 5 |
| 11 | 2.0 | Post | 3 | 5 | 2 | 2 | 2 | 2 | 1 | 5 | 5 | 5 | 4 | 5 |
| 13 | 2.0 | Post | 2 | 2 | 1 | 1 | 0 | 0 | 0 | 3 | 3 | 5 | 1 | 2 |
| | 5.0 | Pre | 2 | 0 | 0 | 0 | 0 | 0 | 0 | 4 | 0 | 4 | 2 | 1 |
| 14 | 1.0 | Pre | 0 | 0 | 0 | 0 | 0 | 0 | 0 | 0 | 0 | — | — | 0 |
| | | Post | 1 | 1 | 0 | 0 | 0 | 0 | 0 | 2 | 0 | 4 | 1 | 3 |
| 14 | 5.0 | Pre | 0 | 3 | 0 | 0 | 0 | 0 | 0 | 3 | 0 | — | — | 3 |
| | | Post | 2 | 2 | 1 | 2 | 1 | 0 | 0 | 3 | 2 | 5 | 1 | 3 |
| 15 | 0.2 | Pre | 0 | 0 | 0 | 0 | 0 | 0 | 0 | 2 | 0 | 0 | 1 | 2 |
| | | Post | 2 | 2 | 0 | 1 | 0 | 0 | 0 | 2 | 1 | 4 | 1 | 3 |
| 15 | 1.0 | Pre | 1 | 0 | 0 | 0 | 0 | 0 | 0 | 4 | 0 | 0 | — | 0 |
| | | Post | 1 | 4 | 1 | 3 | 0 | 0 | 0 | 4 | 3 | 5 | 4 | 4 |
| 15 | 5.0 | Pre | 2 | 5 | 0 | 2 | 1 | 0 | 0 | 5 | 0 | 5 | — | 2 |
| | | Post | 2 | 5 | 1 | 4 | 1 | 1 | 0 | 4 | 3 | 5 | 4 | 4 |
| 17 | 0.5 | Pre | 4 | 5 | 3 | 0 | 1 | 0 | 0 | 4 | 0 | 4 | 1 | 4 |
| | | Post | 2 | 5 | 1 | 1 | 2 | 0 | 0 | 5 | 5 | 5 | 2 | 4 |
| 17 | 1.0 | Pre | 4 | 5 | 3 | 0 | 1 | 0 | 2 | 4 | 2 | 5 | 2 | 4 |
| | | Post | 2 | 5 | 1 | 2 | 2 | 0 | 0 | 5 | 5 | 5 | 3 | 4 |
| 17 | 5.0 | Pre | 5 | 5 | 3 | 1 | 2 | 0 | 2 | 4 | 3 | 5 | 3 | 4 |
| | | Post | 3 | 5 | 4 | 1 | 1 | 0 | 0 | 5 | 5 | 5 | 3 | 4 |
| 18 | 0.5 | Pre | 2 | 4 | — | 0 | 0 | 0 | 0 | 0 | 0 | 3 | 0 | 3 |
| | | Post | 2 | 2 | 1 | 4 | 0 | 0 | 0 | 4 | 4 | — | 2 | 3 |
| 18 | 1.0 | Pre | 1 | 5 | 0 | 0 | 0 | 0 | 0 | 4 | 0 | 4 | 3 | 4 |
| | | Post | 2 | 4 | 2 | 4 | 0 | 0 | 0 | 5 | 4 | — | 2 | 4 |
| 18 | 5.0 | Pre | 2 | 5 | 0 | 1 | 0 | 0 | 0 | 5 | — | 5 | 5 | 5 |
| | | Post | 5 | 5 | 3 | 4 | 0 | 0 | 0 | 5 | 5 | — | 3 | 4 |
| 19 | 5.0 | Pre | 1 | 5 | 1 | 0 | 0 | 0 | 0 | 4 | 0 | 2 | — | 0 |
| | | Post | 1 | 5 | 3 | 0 | 0 | 0 | 0 | 5 | 0 | 5 | — | 2 |
| 20 | 0.25 | Pre | 0 | 5 | 0 | 0 | 0 | 0 | 0 | 4 | 0 | 0 | — | 0 |
| | | Post | 1 | 5 | 4 | 1 | 0 | 0 | 0 | 4 | 5 | 5 | — | 2 |
| 20 | 1.0 | Pre | 2 | 5 | 0 | 0 | 0 | 0 | 0 | 5 | 0 | 1 | 0 | 0 |
| | | Post | 2 | 5 | 3 | 2 | 1 | 0 | 0 | 4 | 5 | 5 | — | 4 |
| 20 | 5.0 | Pre | 5 | 5 | 2 | 1 | 0 | 0 | 0 | 5 | 3 | 5 | — | 5 |
| | | Post | 4 | 5 | 4 | 2 | 1 | 0 | 0 | 5 | 5 | 5 | — | 4 |
| 21 | 0.20 | Pre | 0 | 4 | 0 | 0 | 0 | 0 | 0 | 4 | 0 | 1 | — | 4 |
| | | Post | 4 | 5 | 3 | 0 | 1 | 0 | 0 | 4 | 4 | 5 | 4 | 3 |
| 21 | 1.0 | Pre | 0 | 5 | 0 | 0 | 0 | 0 | 0 | 5 | 0 | 5 | — | 5 |
| | | Post | 3 | 5 | 2 | 2 | 2 | 2 | 0 | 5 | 5 | 5 | 4 | 4 |
| 21 | 5.0 | Pre | 5 | 5 | 0 | 0 | 1 | 0 | 0 | 5 | 5 | 5 | — | 5 |
| | | Post | 5 | 5 | 4 | 3 | 4 | 4 | 0 | 5 | 5 | 5 | 5 | 4 |

TABLE 2-continued

| | | | | | | | | | | | | | | |
|---|---|---|---|---|---|---|---|---|---|---|---|---|---|---|
| 22 | 5 | Pre | 2 | 4 | 0 | 0 | 1 | 0 | 0 | 4 | 2 | 4 | — | 5 |
| | | Post | 5 | 5 | 3 | 2 | 3 | 1 | 3 | 5 | 5 | 5 | 4 | 4 |
| 23 | 5 | Pre | 3 | 5 | 0 | 1 | 0 | 0 | 0 | — | 0 | 4 | — | — |
| | | Post | 3 | 4 | 2 | 2 | 2 | 1 | 1 | 5 | 5 | — | 2 | 4 |
| 24 | 1 | Pre | 5 | 5 | 1 | 1 | 3 | 2 | 2 | 5 | 4 | 5 | — | 5 |
| | | Post | 5 | 5 | 4 | 3 | 4 | 4 | 4 | 5 | 5 | 5 | 5 | 5 |
| 26 | 5 | Pre | 4 | 5 | 1 | 0 | 0 | 0 | 0 | 2 | 0 | 5 | 3 | 5 |
| 27 | 2.5 | Pre | 5 | 5 | 1 | 2 | 2 | 0 | 2 | 5 | 5 | 5 | — | — |
| | | Post | 5 | 5 | 4 | 4 | 4 | 4 | 4 | 5 | 5 | 5 | 5 | 5 |
| 28 | 5 | Pre | 5 | 5 | 1 | 2 | 2 | 0 | 2 | 5 | 5 | 5 | — | — |
| | | Post | 5 | 5 | 4 | — | 4 | 4 | 4 | 5 | 5 | 5 | 5 | 5 |
| 29 | 5 | Pre | 5 | 5 | 4 | 0 | 1 | 0 | 3 | 5 | 5 | 5 | — | 5 |
| | | Post | 5 | 5 | 4 | 1 | 4 | 2 | 5 | 5 | 5 | 5 | 5 | 4 |
| 30 | 5 | Pre | 5 | 5 | 0 | 3 | 4 | 3 | 1 | 5 | 5 | — | — | — |
| | | Post | 5 | 5 | 2 | 4 | 5 | 3 | 4 | 5 | 5 | 5 | — | 5 |
| 31 | 1.0 | Pre | 0 | 3 | 0 | 0 | 0 | 0 | 0 | 3 | 0 | 2 | — | 0 |
| | | Post | 3 | 3 | 0 | 1 | 1 | 2 | 0 | 4 | 3 | 5 | 4 | 3 |
| 32 | 2.0 | Pre | 5 | 5 | 1 | 0 | 1 | 0 | 0 | 5 | 0 | 4 | 3 | 4 |
| | | Post | 3 | 5 | 1 | 2 | 2 | 0 | — | 4 | 5 | 5 | 5 | 4 |
| 33 | 2.0 | Pre | 5 | 5 | 0 | 2 | 4 | 0 | 0 | 5 | 0 | 5 | 5 | 5 |
| | | Post | 5 | 5 | 4 | 4 | 4 | 4 | 5 | 5 | 5 | 5 | 5 | 5 |
| 34 | 0.2 | Pre | 0 | 4 | 0 | 0 | 0 | 0 | 0 | 2 | 0 | 0 | 0 | 0 |
| | | Post | 0 | 4 | 0 | 1 | 0 | 0 | 0 | 5 | 4 | 5 | — | 4 |
| 35 | 4.0 | Pre | 1 | 3 | 0 | 0 | 0 | 0 | 0 | 4 | 0 | 3 | 1 | 2 |
| | | Post | 3 | 5 | 2 | 1 | 0 | 0 | 0 | 4 | 3 | 5 | — | 4 |
| 36 | 5.0 | Pre | 5 | 5 | 2 | 2 | 5 | 5 | 4 | 5 | 5 | 5 | 5 | 5 |
| | | Post | 5 | 5 | 4 | 1 | 5 | 5 | 4 | 5 | 5 | — | 4 | 5 |
| 37 | 5.0 | Pre | 5 | 5 | 1 | 1 | 4 | 4 | 4 | 5 | 0 | 5 | 4 | 3 |
| | | Post | 4 | 5 | 1 | 2 | 4 | 2 | 0 | 5 | 4 | — | 1 | 4 |
| 38 | 4.0 | Pre | 5 | 5 | 4 | 0 | 4 | 4 | 4 | 5 | 4 | 5 | 5 | 5 |
| | | Post | 5 | 5 | 3 | 1 | 5 | 4 | 3 | 5 | 5 | — | 4 | 4 |

| COMPOUND No. | RATE OF APPLICATION kg/ha | PRE- OR POST-EMERGENCE APPLICATION | TEST PLANTS | | | | | | | | | | | |
|---|---|---|---|---|---|---|---|---|---|---|---|---|---|---|
| | | | Po | Xs | Ab | Cv | Ot/Av | Dg | Pu | St | Ec | Sh | Ag | Cn |
| 1 | 0.25 | Pre | 5 | — | 4 | — | 1 | 5 | 1 | 4 | 4 | 5 | 0 | 4 |
| | | Post | — | 5 | 5 | 5 | 0 | 4 | 3 | 5 | 4 | 5 | 0 | — |
| 1 | 1.0 | Pre | 5 | — | 5 | — | 4 | 5 | 3 | 5 | 4 | 5 | 3 | 4 |
| | | Post | — | 5 | 5 | 5 | 4 | 5 | 4 | 5 | 5 | 5 | 0 | — |
| 1 | 5.0 | Pre | 5 | — | 5 | — | 4 | 5 | 4 | 5 | 5 | 5 | 4 | 5 |
| | | Post | — | 5 | 5 | 5 | 5 | 5 | 4 | 5 | 5 | 5 | 3 | — |
| 2 | 0.2 | Pre | 5 | 4 | 5 | — | 0 | 1 | 0 | 2 | 0 | 3 | 0 | 1 |
| | | Post | 2 | 4 | 2 | 3 | 0 | 0 | 2 | 0 | 0 | 3 | 0 | 0 |
| 2 | 1.0 | Pre | 5 | 5 | 5 | — | 1 | 4 | 1 | 4 | 5 | 4 | 1 | 3 |
| | | Post | 4 | 5 | 3 | 5 | 2 | 3 | 3 | 4 | 4 | 5 | 2 | 3 |
| 3 | 0.2 | Pre | 5 | 3 | 2 | — | 0 | 0 | 0 | 0 | 0 | 0 | 1 | 0 |
| | | Post | 2 | 3 | 1 | 5 | 0 | 0 | 0 | 0 | 0 | 0 | 0 | 0 |
| 3 | 1.0 | Pre | 5 | 4 | 5 | — | 0 | 1 | 0 | 1 | 0 | 2 | 1 | 2 |
| | | Post | 2 | 4 | 1 | 4 | 0 | 0 | 0 | 0 | 0 | 3 | 0 | 1 |
| 3 | 5.0 | Pre | 5 | 5 | 5 | — | 1 | 3 | 1 | 4 | 3 | 4 | 2 | 3 |
| 4 | 0.25 | Pre | 5 | — | 2 | — | 0 | 1 | 0 | 1 | 0 | 3 | 0 | 0 |
| | | Post | — | 5 | 4 | 5 | 0 | 4 | 0 | 3 | 3 | 4 | 0 | — |
| 4 | 1.0 | Pre | 5 | — | 4 | — | 0 | 2 | 0 | 1 | 0 | 2 | 0 | 0 |
| | | Post | — | 5 | 5 | 5 | 1 | 3 | 0 | 4 | 1 | 1 | 0 | — |
| 4 | 5.0 | Pre | 5 | — | 5 | — | 0 | 4 | 1 | 2 | 2 | 3 | 0 | 2 |
| | | Post | — | 5 | 5 | 5 | 0 | 4 | 1 | 4 | 4 | 4 | 0 | — |
| 5 | 0.2 | Pre | 5 | 0 | 2 | — | 0 | 0 | 0 | 0 | 0 | 0 | 0 | 0 |
| | | Post | 1 | 1 | 0 | 3 | 0 | 0 | 0 | 0 | 0 | 0 | 0 | 0 |
| 5 | 1.0 | Pre | 5 | 4 | 5 | — | 0 | 0 | 0 | 0 | 0 | 1 | 0 | 0 |
| | | Post | 2 | 3 | 4 | 4 | 0 | 0 | 0 | 0 | 0 | 0 | 0 | 0 |
| 5 | 5.0 | Pre | 5 | 4 | 5 | — | 0 | 1 | 0 | 2 | 0 | 0 | 0 | 0 |
| 6 | 0.2 | Pre | 5 | 0 | 0 | — | 0 | 2 | 0 | 0 | 1 | 0 | 0 | 0 |
| | | Post | 5 | 4 | 4 | 3 | 0 | — | 1 | 5 | 3 | 2 | 0 | 0 |
| 6 | 1.0 | Pre | 5 | 3 | 1 | — | 2 | 3 | 3 | 3 | 4 | 1 | 0 | 0 |
| | | Post | 5 | 4 | 5 | 5 | 1 | — | 4 | 5 | 5 | 3 | 2 | 0 |
| 6 | 5.0 | Post | 5 | 4 | 5 | 5 | 2 | — | 4 | 5 | 5 | 4 | 2 | 0 |
| 7 | 0.25 | Pre | 5 | 2 | 5 | — | 0 | 4 | 0 | 2 | 0 | 3 | 0 | 0 |
| | | Post | 5 | 4 | 1 | 4 | 1 | 4 | 0 | 2 | 1 | 3 | 0 | 0 |
| 7 | 1.0 | Pre | 5 | 5 | 5 | — | 1 | 4 | 1 | 3 | 4 | 4 | 0 | 2 |
| | | Post | 5 | 4 | 3 | 4 | 0 | 4 | 2 | 4 | 1 | 4 | 1 | 4 |
| 7 | 5.0 | Pre | 5 | 5 | 5 | — | 4 | 4 | 4 | 4 | 5 | 4 | 4 | 4 |
| | | Post | 5 | 5 | 5 | 5 | 5 | 5 | 4 | 5 | 5 | 5 | 3 | 4 |
| 8 | 0.2 | Pre | 2 | 0 | 0 | — | 0 | 1 | 0 | 0 | 0 | 0 | 0 | 0 |
| | | Post | 5 | 2 | 4 | 3 | 0 | — | 1 | 5 | 3 | 3 | 0 | 0 |
| 8 | 1.0 | Pre | 4 | 0 | 0 | — | 0 | 2 | 0 | 1 | 0 | 0 | 0 | 0 |
| | | Post | 5 | 3 | 5 | 4 | 1 | — | 1 | 5 | 3 | 4 | 1 | 0 |
| 8 | 5.0 | Pre | 5 | 2 | 3 | — | 0 | 4 | 1 | 3 | 1 | 3 | 2 | 0 |
| | | Post | 5 | 4 | 5 | 4 | 1 | — | 1 | 5 | 5 | 3 | 2 | 0 |
| 9 | 0.25 | Pre | 5 | 0 | 5 | — | 0 | 3 | 0 | 3 | 1 | 1 | 0 | 0 |
| | | Post | 5 | 4 | 4 | 4 | 2 | 2 | 0 | 1 | 0 | 1 | 0 | 0 |
| 9 | 1.0 | Pre | 5 | 1 | 5 | — | 0 | 4 | 0 | 4 | 2 | 3 | 1 | 3 |
| | | Post | 5 | 4 | 5 | 5 | 3 | 5 | 4 | 4 | 3 | 4 | 0 | 1 |

TABLE 2-continued

| | | | | | | | | | | | | | | |
|---|---|---|---|---|---|---|---|---|---|---|---|---|---|---|
| 11 | 2.0 | Post | 5 | 4 | 5 | 5 | 4 | 3 | 0 | 4 | 2 | 3 | 0 | 0 |
| 13 | 2.0 | Post | 3 | 0 | 0 | 4 | 0 | 0 | 0 | 0 | 0 | 0 | 0 | 0 |
|  | 5.0 | Pre | 0 | 4 | 2 | — | 0 | 0 | 0 | 0 | 0 | 0 | 0 | 0 |
| 14 | 1.0 | Pre | 0 | 0 | 0 | — | 0 | 0 | 0 | 0 | 0 | 0 | 0 | 0 |
|  |  | Post | 2 | — | 0 | 3 | 0 | 1 | 0 | 0 | 0 | 0 | 0 | 0 |
| 14 | 5.0 | Pre | 4 | 0 | 4 | — | 0 | 0 | 0 | 0 | 0 | 0 | 0 | 0 |
|  |  | Post | 3 | — | 0 | 3 | 0 | 4 | 0 | 5 | 2 | 1 | 0 | 0 |
| 15 | 0.2 | Pre | 0 | — | 0 | — | 0 | 0 | 0 | 0 | 0 | 0 | 0 | 0 |
|  |  | Post | 0 | — | 1 | 2 | 0 | 0 | 0 | 2 | 0 | 0 | 0 | 0 |
| 15 | 1.0 | Pre | 0 | — | 1 | — | 0 | 1 | 0 | 0 | 0 | 0 | 0 | 0 |
|  |  | Post | 4 | — | 0 | 3 | 0 | 3 | 0 | 4 | 0 | 0 | 0 | 0 |
| 15 | 5.0 | Pre | 4 | — | 4 | — | 0 | 2 | 0 | 2 | 0 | 0 | 0 | 0 |
|  |  | Post | 5 | — | 2 | 4 | 0 | 4 | 0 | 4 | 1 | 3 | 0 | 0 |
| 17 | 0.5 | Pre | 5 | — | 4 | — | 0 | 2 | 0 | 0 | 1 | 1 | 0 | 0 |
|  |  | Post | 5 | 4 | 3 | 5 | 0 | 1 | 0 | 0 | 2 | 0 | 0 | 1 |
| 17 | 1.0 | Pre | 5 | — | 4 | — | 0 | 2 | 0 | 1 | 2 | 1 | 0 | 0 |
|  |  | Post | 5 | 4 | 4 | 5 | 0 | 2 | 0 | 2 | 4 | 0 | 0 | 1 |
| 17 | 5.0 | Pre | 5 | — | 5 | — | 1 | 2 | 0 | 2 | 3 | 1 | 0 | 2 |
|  |  | Post | 5 | 5 | 5 | 5 | 0 | 2 | 0 | 1 | 4 | 0 | 0 | 4 |
| 18 | 0.5 | Pre | 3 | 0 | 1 | — | 0 | 0 | 0 | 0 | 0 | 0 | 1 | 0 |
|  |  | Post | — | 4 | 1 | 5 | 0 | — | 0 | 0 | 0 | 0 | 0 | 0 |
| 18 | 1.0 | Pre | 4 | — | 2 | — | 0 | 0 | 0 | 0 | 0 | 0 | 1 | 0 |
|  |  | Post | — | 4 | 3 | 4 | 0 | — | 0 | 0 | 0 | 0 | 0 | 0 |
| 18 | 5.0 | Pre | 5 | — | 3 | — | 0 | 3 | 0 | 0 | 0 | 2 | 3 | 1 |
|  |  | Post | — | 4 | 4 | 5 | 0 | — | 0 | 0 | 1 | 0 | 0 | 1 |
| 19 | 5.0 | Pre | 2 | — | 5 | — | 0 | 0 | 0 | 0 | 0 | 0 | 0 | 0 |
|  |  | Post | 5 | 2 | 2 | 4 | 0 | 0 | 0 | 0 | 0 | 0 | 0 | 0 |
| 20 | 0.25 | Pre | 0 | — | 3 | — | 0 | 0 | 0 | 0 | 0 | 0 | 0 | 0 |
|  |  | Post | 5 | 3 | 4 | 5 | 0 | 0 | 0 | 1 | 0 | 0 | 0 | 0 |
| 20 | 1.0 | Pre | 5 | — | 4 | — | 0 | 0 | 0 | 0 | 0 | 0 | 0 | 1 |
|  |  | Post | 5 | 4 | 5 | 5 | 0 | 0 | 0 | 2 | 0 | 0 | 0 | 4 |
| 20 | 5.0 | Pre | 5 | — | 5 | — | 0 | 0 | 0 | 0 | 0 | 0 | 0 | 3 |
|  |  | Post | 5 | 5 | 5 | 5 | 0 | 1 | 0 | 2 | 2 | 0 | 0 | 4 |
| 21 | 0.20 | Pre | 5 | 0 | 3 | — | 0 | 0 | 0 | 0 | 0 | 0 | 0 | 0 |
|  |  | Post | 4 | 2 | 2 | 4 | 0 | 1 | 0 | 5 | 2 | 1 | 0 | 0 |
| 21 | 1.0 | Pre | 5 | 0 | 5 | — | 0 | 0 | 0 | 0 | 0 | 0 | 0 | 0 |
|  |  | Post | 5 | 4 | 4 | 4 | 0 | 0 | 2 | 4 | 5 | 3 | 0 | 2 |
| 21 | 5.0 | Pre | 5 | 1 | 5 | — | 0 | 0 | 0 | 1 | 3 | 0 | 0 | 1 |
|  |  | Post | 5 | 4 | 5 | 5 | 2 | 3 | 2 | 5 | 5 | 5 | 2 | 1 |
| 22 | 5 | Pre | 5 | 3 | 3 | — | 0 | 2 | 0 | 2 | 1 | 0 | 0 | 0 |
|  |  | Post | 5 | 5 | 3 | 5 | 0 | 5 | 1 | 4 | 4 | 3 | 0 | 0 |
| 23 | 5 | Pre | 5 | 0 | 4 | — | 0 | 2 | 1 | 0 | 1 | 0 | 0 | 0 |
|  |  | Post | 5 | 3 | 4 | 4 | 0 | 3 | 2 | 3 | 4 | 1 | 0 | 0 |
| 24 | 1 | Pre | 5 | 4 | 4 | — | 2 | 3 | 3 | 4 | 4 | 5 | 3 | — |
|  |  | Post | 5 | 5 | 5 | 5 | 4 | 5 | 5 | 5 | 5 | 5 | 4 | 4 |
| 26 | 5 | Pre | 5 | 5 | 4 | — | 0 | 0 | 0 | 2 | 0 | 1 | 1 | 0 |
| 27 | 2.5 | Pre | 5 | 3 | 4 | — | 0 | — | 1 | 2 | 3 | 3 | 1 | — |
|  |  | Post | 5 | 5 | 5 | 5 | 3 | 5 | 4 | 5 | 5 | 5 | 4 | 3 |
| 28 | 5 | Pre | 5 | 4 | 4 | — | 0 | — | 0 | 2 | 2 | 2 | 1 | — |
|  |  | Post | 5 | 5 | 5 | 5 | 1 | 5 | 2 | 4 | 5 | 4 | 0 | 0 |
| 29 | 5 | Pre | 5 | 5 | 5 | — | 0 | 3 | 0 | 4 | 4 | 1 | 1 | 3 |
|  |  | Post | 5 | 5 | 5 | 5 | 2 | — | 2 | 5 | 5 | 5 | 3 | 4 |
| 30 | 5 | Pre | 5 | 3 | 5 | — | 0 | 5 | 3 | 5 | 4 | 5 | 2 | 1 |
|  |  | Post | 5 | 4 | 5 | 5 | 3 | 5 | 5 | 5 | 5 | 5 | 2 | — |
| 31 | 1.0 | Pre | 4 | 2 | 1 | — | 0 | 0 | 0 | 0 | 0 | 0 | 0 | 0 |
|  |  | Post | 3 | 2 | 2 | 3 | 0 | 0 | 0 | 3 | 2 | — | 0 | 1 |
| 32 | 2.0 | Pre | 5 | 0 | — | — | 0 | 1 | 0 | 0 | 0 | 0 | 1 | 1 |
|  |  | Post | 5 | 2 | 3 | 4 | 0 | 1 | 0 | 4 | 2 | 1 | 0 | 0 |
| 33 | 2.0 | Pre | 5 | 4 | — | — | 2 | 4 | 4 | 4 | 2 | 3 | 4 | 0 |
|  |  | Post | 5 | 5 | 5 | 5 | 5 | 5 | 4 | 5 | 4 | 5 | 4 | 3 |
| 34 | 0.2 | Pre | 5 | 0 | 2 | — | 0 | 0 | 0 | 0 | 0 | 0 | 0 | 0 |
|  |  | Post | 5 | 0 | 1 | 3 | 0 | 0 | 0 | 0 | 4 | — | 0 | 0 |
| 35 | 4.0 | Pre | 1 | 0 | 4 | — | 0 | 0 | 0 | 0 | 0 | 0 | 0 | 0 |
|  |  | Post | 4 | 2 | 2 | 3 | 0 | 0 | 0 | 0 | 0 | — | 0 | 0 |
| 36 | 5.0 | Pre | 5 | 5 | 5 | — | 4 | 5 | 3 | 5 | 5 | 5 | 5 | 4 |
|  |  | Post | 5 | 5 | 5 | 5 | 5 | 5 | 4 | 5 | 5 | 5 | 4 | 4 |
| 37 | 5.0 | Pre | 4 | 2 | 4 | — | 3 | 4 | 0 | 5 | 1 | 2 | 2 | 0 |
|  |  | Post | 4 | 4 | 4 | 3 | 2 | 5 | 0 | 3 | 4 | 4 | 0 | 0 |
| 38 | 4.0 | Pre | 5 | 5 | 5 | — | 4 | 5 | 2 | 5 | 5 | 5 | 5 | 4 |
|  |  | Post | 5 | 5 | 5 | 5 | 4 | 5 | 2 | 5 | 5 | 5 | 2 | 2 |

Names of test plants in Table 2

| | |
|---|---|
| Sb | Sugar beet |
| Rp | Rape |
| Ct | Cotton |
| Sy | Soya bean |
| Mz | Maize |
| Ww | Winter wheat |
| Rc | Rice |
| Sn | *Senecio vulgaris* |
| Ip | *Ipomoea purpurea* |
| Am | *Amaranthus retroflexus* |
| Pi | *Polygonum aviculare* |
| Ca | *Chenopodium album* |
| Po | *Portulaca oleracea* |
| Xs | *Xanthium spinosum* |

-continued

Names of test plants in Table 2

| | |
|---|---|
| Ab | *Abutilon theophrastii* |
| Cv | *Convolvulus arvenis* |
| Ot/Av | Oats (cultivated in pre-emergence test and *Avena fatua* (wild oats) in post-emergence test) |
| Dg | *Digitaria sanguinalis* |
| Pu | *Poa annua* |
| St | *Setaria viridis* |
| Ec | *Echinochloa crus-galli* |
| Sh | *Sorghum halepense* |
| Ag | *Agropyron repens* |
| Cn | *Cyperus rotundus* |

EXAMPLE 14

This Example further illustrates the herbicidal properties of compounds according to the invention. Tests were carried out as described in Example 13, but using a different range of test plants. The post-emergence test was slightly different from the one described in Example 13 in that the seeds were sown in trays of soil and covered with a few millimeters of soil before spraying the test compound, whereas in the previous test the seeds were sprayed directly.

The compounds were formulated in a similar way to that described in Example 13, but using a cyclohexanone solution containing Synperonic NPE 1800 (a nonyl-phenolpropylene oxide-ethylene oxide condensate) and Tween 85 (a condensate of sorbitan tri-oleate with 20 molar proportions of ethylene oxide) instead of the methylcyclohexanone solution of surfactants described in that Example. The damage of the test plants was assessed on a scale of 0 to 9 where 0 represents 0 to 10% damage to the plant and 9 is 90 to 100% damage. Assessments were made 26 days after spraying the compounds. The results are given in Table 3 below.

| | |
|---|---|
| Bt | *Bromus tectorum* |
| Ag | *Agropyron repens* |
| Ga | *Galium aparine* |
| Sm | *Stellaria media* |
| Ca | *Chenopodium album* |
| Pi | *Polygonum aviculare* |
| Ma | *Matricaria inodora* |
| Sp | *Sinapis alba* |

EXAMPLE 15

This Example illustrates a composition according to the invention comprising a dispersible powder.

The following ingredients were ground up together to form a finely divided powder.

| Constituent | Percentage by weight |
|---|---|
| Compound No. 1 | 50 |
| Vanisperse CB | 5 |
| Aerosol OTB | 2 |
| China clay GT-Y | to 100 percent |

Vanisperse CB comprises sodium lignosulphonate Aerosol OT-B comprises sodium dioctylsulphosuccinate.

EXAMPLE 16

This Example illustrates a soluble powder composition according to the invention. The following ingredients were ground together in the proportions specified.

| Constituent | Percentage by weight |
|---|---|
| Compound No. 1 | 50 |
| Sodium carbonate | to 100 percent |

TABLE 3

| COMPOUND No. | RATE OF APPLICATION kg/ha | PRE-OR POST-EMERGENCE APPLICATION | Ww | Br | Pe | Rp | Sb | Lt | Av | Al | Bt | Ag | Ga | Sm | Ca | Pi | Ma | Sp |
|---|---|---|---|---|---|---|---|---|---|---|---|---|---|---|---|---|---|---|
| 7 | 0.25 | Post | 0 | 4 | 2 | 9 | 9 | 9 | 1 | 3 | 2 | 3 | 6 | 8 | 8 | 7 | 9 | 9 |
|   | 0.5 | Post | 3 | 2 | 6 | 9 | 9 | 9 | 1 | 3 | 3 | 4 | 8 | 9 | 8 | 8 | 9 | 9 |
|   | 1.0 | Post | 6 | 9 | 7 | 9 | 9 | 9 | 3 | 8 | 5 | 5 | 9 | 9 | 9 | 9 | 9 | 9 |
| 7 | 0.25 | Pre | 0 | 1 | 1 | 9 | 9 | 9 | 0 | 5 | 3 | 1 | 5 | 9 | 9 | — | 9 | 8 |
|   | 0.5 | Pre | 4 | 3 | 1 | 9 | 9 | 9 | 0 | 5 | 4 | 1 | 7 | 9 | 9 | — | 9 | 9 |
|   | 1.0 | Pre | 7 | 4 | 7 | 9 | 9 | 9 | 6 | 7 | 8 | 4 | 9 | 9 | 9 | — | 9 | 9 |
| 9 | 0.25 | Post | 1 | 1 | 4 | 9 | 5 | 9 | 1 | 2 | 2 | 2 | 2 | 5 | 9 | 8 | 9 | 9 |
|   | 0.5 | Post | 2 | 2 | 5 | 9 | 9 | 9 | 0 | 3 | 3 | 2 | 7 | 9 | 9 | 9 | 9 | 9 |
|   | 1.0 | Post | 5 | 6 | 6 | 9 | 9 | 9 | 1 | 6 | 5 | 4 | 9 | 9 | 9 | 9 | 9 | 9 |
| 9 | 0.25 | Pre | 0 | 1 | 1 | 7 | 9 | 9 | 0 | 1 | 3 | 2 | 2 | 5 | 9 | — | 8 | 6 |
|   | 0.5 | Pre | 0 | 1 | 0 | 9 | 9 | 9 | 1 | 4 | 4 | 3 | 6 | 8 | 9 | — | 9 | 8 |
|   | 1.0 | Pre | 7 | 5 | 0 | 9 | 9 | 9 | 2 | 6 | 7 | 3 | 9 | 9 | 9 | — | 9 | 9 |
| 17 | 0.25 | Post | 0 | 1 | 1 | 9 | 0 | 7 | 0 | 0 | 0 | 0 | — | 0 | 7 | 1 | 8 | 7 |
|   | 0.5 | Post | 0 | 0 | 0 | 9 | 0 | 9 | 0 | 0 | 0 | 0 | — | 0 | 8 | 1 | 7 | 9 |
|   | 1.0 | Post | 0 | 0 | 0 | 9 | 9 | 9 | 0 | 0 | 0 | 0 | — | 0 | 9 | 2 | 9 | 9 |
| 17 | 0.25 | Pre | 0 | 0 | 0 | 9 | 1 | 8 | 0 | 0 | 0 | — | 1 | 3 | 3 | 7 | 9 | 2 |
|   | 0.5 | Pre | 1 | 0 | 1 | 9 | 5 | 9 | 0 | 0 | 0 | — | 4 | 6 | 7 | 8 | 9 | 5 |
|   | 1.0 | Pre | 1 | 0 | 0 | 9 | 9 | 9 | 1 | 0 | 0 | — | 6 | 7 | 7 | 9 | 9 | 7 |

The names of the test plants in Table 3 are as follows:

| | |
|---|---|
| Ww | Winter wheat |
| Br | Barley |
| Pe | Peas |
| Rp | Rape |
| Sb | Sugar beet |
| Lt | Lettuce |
| Av | *Avena fatua* |
| Al | *Alopecurus myosuroides* |

The soluble powder may be formulated as soluble granules by adding water to the powder and mixing to convert it to a paste, and then extruding the paste through suitably sized dies to produce granules which harden on standing for a time.

This formulation may also optionally contain a surface-active agent, for example the condensation product of p-nonylphenol with from 7 to 8 molar proportions of ethylene oxide.

EXAMPLE 17

This Example illustrates a composition according to the invention comprising an aqueous dispersion. The following ingredients were ground together to give an aqueous dispersion

| Constituent | Percentage by weight |
| --- | --- |
| Compound No. 1 | 50 |
| Synperonic NP13 | 1.25 |
| Polyfon H | 5 |
| Water | to 100 percent |

Synperonic NP13 comprises a condensate of p-nonylphenol with 13 molar proportions of ethylene oxide.

Polyfon H comprises sodium lignosulphonate.

EXAMPLE 18

This Example illustrates a composition according to the invention comprising an aqueous solution. The following ingredients were mixed to give an aqueous solution.

| Constituent | Amount (grams per liter) |
| --- | --- |
| Compound No. 1 | 200 |
| Sodium carbonate solution (5%) | 484 |
| Water | to 1 liter |

If desired, a surface-active agent may be included in this composition.

EXAMPLE 19

This Example illustrates a composition according to the invention comprising a non-aqueous solution. The following ingredients were mixed together.

| Constituent | Amount (grams per liter) |
| --- | --- |
| Compound No. 1 | 350 |
| Triethanolamine | 40 |
| Synperonic A20 | 17 |
| Cyclohexanone | to 1 liter |

Synperonic A20 comprises a mixture of straight and branched chain $C_{13}$ to $C_{15}$ alcohols condensed with twenty molar proportions of ethylene oxide.

EXAMPLE 20

This Example illustrates a composition according to the invention comprising an emulsifiable concentrate. The following ingredients were mixed together in the proportions specified.

| Constituent | Amount (grams per liter) |
| --- | --- |
| Compound No. 7 | 250 |
| Armeen 12D | 105 |
| Synperonic NPE1800 | 50 |
| Aromasol | to 1 liter |

Armeen 12D comprises a $C_{12}$ Primary amine. Synperonic NPE1800 comprises a nonylphenol-propylene oxide-ethylene oxide block copolymer.

EXAMPLE 21

This Example illustrates a composition according to the invention which comprises a non-aqueous dispersion. The following ingredients were wet-milled together in the stated proportions.

| Constituent | Amount (grams per liter) |
| --- | --- |
| Compound No. 7 | 250 |
| Triton B1956 | 50 |
| Isopar L | to 1 liter |

Triton B1956 comprises a 70% solution of a modified phthalic glycerol alkyl resin in 1,2-dichloroethane. Isopar L comprises a mixture of branched saturated aliphatic hydrocarbons. This composition may be used for ultra-low volume spraying.

EXAMPLE 22

This Example describes a comparative test of the herbicidal effect of the two polymorphic forms of solid compound no. 1. In this example, the form with carbonyl infra-red absorption at 1680 cm$^{-1}$ is referred to as Form A and the form with absorption at 1708 cm$^{-1}$ is referred to as Form B.

Forms A and B were each formulated as a dispersible powder and as a flowable paste of the finely ground solid dispersed in water. The dispersible powder formulation contained 50% by weight of the active ingredient together with Vanisperse CB (5% by weight; this material comprises sodium lignosulphonate) and Aerosol OTB (2% by weight; this is a dry wetting agent comprising diisoctylsulphosuccinate), the balance to 100% being china clay GTY.

The flowable paste contained 40% by weight of active ingredient, together with 1% by weight of Synperonic NP13 (a surface-active agent comprising a condensate of 13 molar proportions of ethylene oxide with p-nonylphenol) and 4% of Polyfon H (a dispersing agent comprising sodium lignosulphonate) the balance to 100% being water.

The formulations were made up to a dilution corresponding to a spray volume of 200 liters per hectare. The final spray solution contained 0.1% of Agral 90 (Agral 90 is a solution of a condensate of p-nonylphenol with from 7 to 8 molar proportions of ethylene oxide in ethanol).

The spray solutions were applied to plants grown in the greenhouse, at the 2 to 5 leaf stage of development. The damage to the plants was assessed 20 days after treatment, on a scale of 0 to 9 where 0 is 0 to 10% damage and 9 is 90 to 100%. The results of the tests are given in Tables 3 and 4. Table 3 gives the results for the dispersible powder formulation and Table 4 for the flowable paste.

TABLE 3

| ACTIVE INGREDIENT | RATE OF APPLICATION kg/ha | TEST PLANTS | | | | TOTAL SCORE |
| --- | --- | --- | --- | --- | --- | --- |
| | | Ip | Ab | Ec | Dg | |
| A | 0.1 | 3 | 7 | 1 | 2 | 13 |
| A | 0.2 | 7 | 9 | 4 | 5 | 25 |
| A | 0.4 | 8 | 9 | 6 | 7 | 30 |
| B | 0.1 | 3 | 7 | 1 | 2 | 13 |
| B | 0.2 | 7 | 8 | 2 | 4 | 21 |
| B | 0.4 | 6 | 9 | 5 | 8 | 28 |

TABLE 4

| ACTIVE INGREDIENT | RATE OF APPLICATION kg/ha | TEST PLANTS | | | | TOTAL SCORE |
|---|---|---|---|---|---|---|
| | | Ip | Ab | Ec | Dg | |
| A | 0.1 | 4 | 8 | 2 | 2 | 16 |
| A | 0.2 | 5 | 8 | 3 | 5 | 21 |
| A | 0.4 | 8 | 9 | 5 | 8 | 30 |
| B | 0.1 | 2 | 5 | 2 | 2 | 11 |
| B | 0.2 | 6 | 8 | 3 | 4 | 21 |
| B | 0.4 | 7 | 8 | 5 | 8 | 28 |

The names of the test plants in Tables 3 and 4 are as follows:

| Ip | Ipomoea purpurea |
| Ab | Abutilon theophrasti |
| Ec | Echinochloa crus-galli |
| Dg | Digitaria sanguinalis |

Within the limits of accuracy inherent in a biological test of this kind, the herbicidal effects of the two polymorphic forms were identical.

We claim:

1. Herbicidal diphenyl ether compounds of the formula (I)

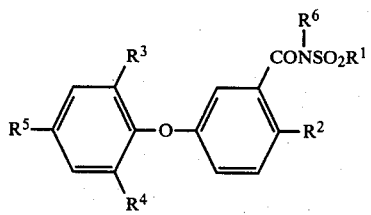

and salts thereof,
wherein $R^1$ is an alkyl group of 1 to 6 carbon atoms optionally substituted by one or more fluorine atoms, or by a phenyl group optionally substituted by one or more halogen atoms; $R^2$ is a hydrogen atom, a fluorine, chlorine, bromine, or iodine atom, or a nitro group; $R^3$ is a hydrogen atom, a fluorine, chlorine, bromine, or iodine atom, an alkyl group of 1 to 6 carbon atoms, a trifluoromethyl group, or a cyano group; $R^4$ is a hydrogen atom, a fluorine, chlorine, bromine, or iodine atom, or a trifluoromethyl group; $R^5$ is a fluorine, chlorine, bromine, or iodine atom or a trifluoromethyl group; and $R^6$ is a hydrogen atom or an alkyl group of 1 to 4 carbon atoms.

2. Herbicidal diphenyl ether compounds as claimed in claim 1 wherein $R^1$ is a methyl or ethyl group; $R^2$ is a nitro group; $R^3$ is a chlorine atom; $R^4$ is a hydrogen atom, $R^5$ is a chlorine atom or a trifluoromethyl group; and $R^6$ is a hydrogen atom.

3. Herbicidal compounds as claimed in claim 1 wherein $R^1$ is a methyl group; $R^2$ is a chlorine or bromine atom; $R^3$ is a chlorine atom; $R^4$ is a hydrogen atom; $R^5$ is a chlorine atom or a trifluoromethyl group; and $R^6$ is a hydrogen atom.

4. The compound as claimed in claim 1 wherein $R^1$ is a methyl group; $R^2$ is a nitro group; $R^3$ is a chlorine atom; $R^4$ is a hydrogen atom; $R^5$ is a trifluoromethyl group; and $R^6$ is a hydrogen atom.

5. The compound as claimed in claim 1 wherein $R^1$ is a methyl group; $R^2$ is a chlorine atom; $R^3$ is a chlorine atom; $R^4$ is a hydrogen atom; $R^5$ is a trifluoromethyl group; and $R^6$ is a hydrogen atom.

6. A process of killing or severely damaging unwanted plants, which comprises applying to the plants, or to the locus thereof, a compound of the formula (I) or a salt thereof as defined in claim 1.

7. A process of selectively controlling the growth of weeds in crops of cotton, which comprises applying to the crop area, in an amount sufficient to control the growth of the weeds, but insufficient to damage the crop substantially, a compound of the formula (I) defined in claim 1.

8. A process of selectively controlling weeds in crops of soya bean, which comprises applying to the crop area, in an amount sufficient to control the weeds but insufficient to damage the crop substantially, a compound of the formula defined in claim 2.

9. Herbicidal compositions, comprising as an active ingredient a compound of the formula I or a salt thereof, as defined in claim 1, in admixture with a carrier comprising a solid or liquid diluent.

* * * * *